United States Patent
Laurent et al.

(10) Patent No.: US 9,675,372 B2
(45) Date of Patent: Jun. 13, 2017

(54) MOTOR-DRIVEN SURGICAL CUTTING INSTRUMENT WITH ELECTRIC ACTUATOR DIRECTIONAL CONTROL ASSEMBLY

(71) Applicant: Ethicon Endo-Surgery, Inc., Cincinnati, OH (US)

(72) Inventors: Ryan J. Laurent, Liberty Township, OH (US); Brett E. Swensgard, West Chester, OH (US); Bret W. Smith, Kings Mills, OH (US)

(73) Assignee: Ethicon LLC, Guaynabo, PR (US)

( * ) Notice: Subject to any disclaimer, the term of this patent is extended or adjusted under 35 U.S.C. 154(b) by 826 days.

(21) Appl. No.: 13/902,249

(22) Filed: May 24, 2013

(65) Prior Publication Data

US 2013/0261648 A1 Oct. 3, 2013

Related U.S. Application Data

(63) Continuation of application No. 13/482,179, filed on May 29, 2012, now Pat. No. 8,453,914, which is a
(Continued)

(51) Int. Cl.
*A61B 17/04* (2006.01)
*A61B 17/10* (2006.01)
(Continued)

(52) U.S. Cl.
CPC .... *A61B 17/320016* (2013.01); *A61B 17/068* (2013.01); *A61B 17/072* (2013.01);
(Continued)

(58) Field of Classification Search
CPC ............ A61B 17/320016; A61B 17/68; A61B 2017/00398; A61B 2017/00017; A61B 2017/00039
(Continued)

(56) References Cited

U.S. PATENT DOCUMENTS 2,853,074 A 9/1958 Olson
3,078,465 A 2/1963 Bobrov
(Continued)

FOREIGN PATENT DOCUMENTS

CA 2458946 A1 3/2003
CA 2512960 A1 1/2006
(Continued)

OTHER PUBLICATIONS

International Search Report for PCT/US2010/059141, dated Feb. 28, 2011, included in PCT Publication No. WO 2011/078960 (60 pages).
(Continued)

*Primary Examiner* — Robert Long

(57) ABSTRACT

A motor-driven surgical instrument that may comprise (i) a moveable drive member that is driven in a first direction when the electric motor operates in a first direction and that is driven in a second direction when the electric motor operates in a second direction. Movement of the drive member causes movement of the moveable component of the end effector, and (ii) a motor control circuit connected to the motor for controlling the motor. The motor control circuit may comprise a switching circuit that, upon actuation, reverses the direction of the motor from the first direction to the second direction. The switching circuit may be actuatable separately through each of: (i) actuation of a moveable actuator of the switching circuit through movement of the drive member at least in the first direction; and (ii) manual actuation by a user of the surgical instrument.

13 Claims, 34 Drawing Sheets

Related U.S. Application Data continuation of application No. 12/647,100, filed on Dec. 24, 2009, now Pat. No. 8,220,688.

(51) Int. Cl.

| | | |
|---|---|---|
| A61B 17/32 | (2006.01) | |
| A61B 17/068 | (2006.01) | |
| A61B 17/072 | (2006.01) | |
| H01H 3/16 | (2006.01) | |
| H01H 13/18 | (2006.01) | |
| A61B 17/00 | (2006.01) | |

(52) U.S. Cl.
CPC .............. *H01H 3/16* (2013.01); *H01H 13/18* (2013.01); *A61B 2017/00017* (2013.01); *Y10T 74/18976* (2015.01)

(58) Field of Classification Search
USPC .......................................... 227/175.1–182.1
See application file for complete search history.

(56) References Cited

U.S. PATENT DOCUMENTS

| | | |
|---|---|---|
| 3,079,606 A | 3/1963 | Bobrov et al. |
| 3,080,564 A | 3/1963 | Strekopitov et al. |
| 3,269,630 A | 8/1966 | Fleischer |
| 3,269,631 A | 8/1966 | Takaro |
| 3,480,193 A | 11/1969 | Ralston |
| 3,490,675 A | 1/1970 | Green et al. |
| 3,499,591 A | 3/1970 | Green |
| 3,551,987 A | 1/1971 | Wilkinson |
| 3,589,589 A | 6/1971 | Akopov |
| 3,618,842 A | 11/1971 | Bryan |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| 3,837,555 A | 9/1974 | Green |
| RE28,932 E | 8/1976 | Noiles et al. |
| 4,127,227 A | 11/1978 | Green |
| 4,296,881 A | 10/1981 | Lee |
| 4,331,277 A | 5/1982 | Green |
| 4,380,312 A | 4/1983 | Landrus |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,414 A | 3/1985 | Filipi |
| 4,506,671 A | 3/1985 | Green |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,915,100 A | 4/1990 | Green |
| 4,930,503 A | 6/1990 | Pruitt |
| 4,941,623 A | 7/1990 | Pruitt |
| 4,944,443 A | 7/1990 | Oddsen et al. |
| 4,951,860 A | 8/1990 | Peters et al. |
| 4,951,861 A | 8/1990 | Schulze et al. |
| 4,955,959 A | 9/1990 | Tompkins et al. |
| 4,962,877 A | 10/1990 | Hervas |
| 4,964,559 A | 10/1990 | Deniega et al. |
| 4,978,049 A | 12/1990 | Green |
| 5,005,754 A | 4/1991 | Van Overloop |
| 5,014,898 A | 5/1991 | Heidrich |
| 5,014,899 A | 5/1991 | Presty et al. |
| 5,018,657 A | 5/1991 | Pedlick et al. |
| 5,040,715 A | 8/1991 | Green et al. |
| 5,062,563 A | 11/1991 | Green et al. |
| 5,065,929 A | 11/1991 | Schulze et al. |
| 5,071,052 A | 12/1991 | Rodak et al. |
| 5,074,454 A | 12/1991 | Peters |
| 5,098,004 A | 3/1992 | Kerrigan |
| 5,100,042 A | 3/1992 | Gravener et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,137,198 A | 8/1992 | Nobis et al. |
| 5,141,144 A | 8/1992 | Foslien et al. |
| 5,156,315 A | 10/1992 | Green et al. |
| 5,163,598 A | 11/1992 | Peters et al. |
| 5,197,648 A | 3/1993 | Gingold |
| 5,205,459 A | 4/1993 | Brinkerhoff et al. |
| 5,219,111 A | 6/1993 | Bilotti et al. |
| 5,221,036 A | 6/1993 | Takase |
| 5,240,163 A | 8/1993 | Stein et al. |
| 5,246,156 A | 9/1993 | Rothfuss et al. |
| 5,253,793 A | 10/1993 | Green et al. |
| 5,263,629 A | 11/1993 | Trumbull et al. |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,285,945 A | 2/1994 | Brinkerhoff et al. |
| 5,289,963 A | 3/1994 | McGarry et al. |
| 5,297,714 A | 3/1994 | Kramer |
| 5,307,976 A | 5/1994 | Olson et al. |
| 5,312,023 A | 5/1994 | Green et al. |
| 5,312,024 A | 5/1994 | Grant et al. |
| 5,318,221 A | 6/1994 | Green et al. |
| 5,326,013 A | 7/1994 | Green et al. |
| 5,332,142 A | 7/1994 | Robinson et al. |
| 5,344,059 A | 9/1994 | Green et al. |
| 5,344,060 A | 9/1994 | Gravener et al. |
| 5,356,064 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,379,933 A | 1/1995 | Green et al. |
| 5,381,943 A | 1/1995 | Allen et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,397,046 A | 3/1995 | Savage et al. |
| 5,403,312 A | 4/1995 | Yates et al. |
| 5,405,072 A | 4/1995 | Zlock et al. |
| 5,405,073 A | 4/1995 | Porter |
| 5,413,267 A | 5/1995 | Solyntjes et al. |
| 5,413,268 A | 5/1995 | Green et al. |
| 5,413,272 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |

(56) References Cited

U.S. PATENT DOCUMENTS

| | | |
|---|---|---|
| 5,431,322 A | 7/1995 | Green et al. |
| 5,431,323 A | 7/1995 | Smith et al. |
| 5,433,721 A | 7/1995 | Hooven et al. |
| 5,439,156 A | 8/1995 | Grant et al. |
| 5,441,193 A | 8/1995 | Gravener |
| 5,443,197 A | 8/1995 | Malis et al. |
| 5,445,304 A | 8/1995 | Plyley et al. |
| 5,447,265 A | 9/1995 | Vidal et al. |
| 5,452,836 A | 9/1995 | Huitema et al. |
| 5,452,837 A | 9/1995 | Williamson, IV et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,465,895 A | 11/1995 | Knodel et al. |
| 5,465,896 A | 11/1995 | Allen et al. |
| 5,467,911 A | 11/1995 | Tsuruta et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,505,363 A | 4/1996 | Green et al. |
| 5,507,426 A | 4/1996 | Young et al. |
| 5,509,596 A | 4/1996 | Green et al. |
| 5,529,235 A | 6/1996 | Boiarski et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,547,117 A | 8/1996 | Hamblin et al. |
| 5,553,765 A | 9/1996 | Knodel et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,564,615 A | 10/1996 | Bishop et al. |
| 5,577,654 A | 11/1996 | Bishop |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,697,543 A | 12/1997 | Burdorff |
| 5,704,534 A | 1/1998 | Huitema et al. |
| 5,706,997 A | 1/1998 | Green et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,715,988 A | 2/1998 | Palmer |
| 5,718,359 A | 2/1998 | Palmer et al. |
| 5,718,360 A | 2/1998 | Green et al. |
| 5,732,871 A | 3/1998 | Clark et al. |
| 5,732,872 A | 3/1998 | Bolduc et al. |
| 5,735,445 A | 4/1998 | Vidal et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,255 A | 6/1998 | Chrisman et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,816,471 A | 10/1998 | Plyley et al. |
| 5,820,009 A | 10/1998 | Melling et al. |
| 5,826,776 A | 10/1998 | Schulze et al. |
| 5,829,662 A | 11/1998 | Allen et al. |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,871,135 A | 2/1999 | Williamson, IV et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,911,353 A | 6/1999 | Bolanos et al. |
| 5,915,616 A | 6/1999 | Viola et al. |
| 5,918,791 A | 7/1999 | Sorrentino et al. |
| 5,937,951 A | 8/1999 | Izuchukwu et al. |
| 5,941,442 A | 8/1999 | Geiste et al. |
| 5,954,259 A | 9/1999 | Viola et al. |
| 5,988,479 A | 11/1999 | Palmer |
| 6,010,054 A | 1/2000 | Johnson et al. |
| 6,032,849 A | 3/2000 | Mastri et al. |
| 6,047,861 A | 4/2000 | Vidal et al. |
| 6,050,472 A | 4/2000 | Shibata |

(56) References Cited

U.S. PATENT DOCUMENTS

| | | |
|---|---|---|
| 6,053,390 A | 4/2000 | Green et al. |
| 6,079,606 A | 6/2000 | Milliman et al. |
| 6,102,271 A | 8/2000 | Longo et al. |
| 6,109,500 A | 8/2000 | Alli et al. |
| 6,119,913 A | 9/2000 | Adams et al. |
| 6,126,058 A | 10/2000 | Adams et al. |
| 6,131,789 A | 10/2000 | Schulze et al. |
| 6,155,473 A | 12/2000 | Tompkins et al. |
| 6,193,129 B1 | 2/2001 | Bittner et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,330,965 B1 | 12/2001 | Milliman et al. |
| 6,439,446 B1 | 8/2002 | Perry et al. |
| 6,450,391 B1 | 9/2002 | Kayan et al. |
| 6,488,196 B1 | 12/2002 | Fenton, Jr. |
| 6,488,197 B1 | 12/2002 | Whitman |
| 6,491,201 B1 | 12/2002 | Whitman |
| 6,505,768 B2 | 1/2003 | Whitman |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,619,529 B2 | 9/2003 | Green et al. |
| 6,629,630 B2 | 10/2003 | Adams |
| 6,644,532 B2 | 11/2003 | Green et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,705,503 B1 | 3/2004 | Pedicini et al. |
| 6,722,552 B2 | 4/2004 | Fenton, Jr. |
| 6,755,338 B2 | 6/2004 | Hahnen et al. |
| 6,769,594 B2 | 8/2004 | Orban, III |
| 6,786,382 B1 | 9/2004 | Hoffman |
| 6,793,652 B1 * | 9/2004 | Whitman ............ A61B 10/0233 128/898 |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| RE38,708 E | 3/2005 | Bolanos et al. |
| 6,866,178 B2 | 3/2005 | Adams et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,080,769 B2 | 7/2006 | Vresh et al. |
| 7,083,073 B2 | 8/2006 | Yoshie et al. |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,213,736 B2 | 5/2007 | Wales et al. |
| 7,225,963 B2 | 6/2007 | Scirica |
| 7,225,964 B2 | 6/2007 | Mastri et al. |
| 7,234,624 B2 | 6/2007 | Gresham et al. |
| 7,237,708 B1 | 7/2007 | Guy et al. |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,481,347 B2 | 1/2009 | Roy |
| 7,481,349 B2 | 1/2009 | Holsten et al. |
| 7,490,749 B2 | 2/2009 | Schall et al. |
| 7,494,039 B2 | 2/2009 | Racenet et al. |
| 7,500,979 B2 | 3/2009 | Hueil et al. |

(56) References Cited

U.S. PATENT DOCUMENTS

| | | |
|---|---|---|
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,549,563 B2 | 6/2009 | Mather et al. |
| 7,549,564 B2 | 6/2009 | Boudreaux |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,624,902 B2 | 12/2009 | Marczyk et al. |
| 7,631,793 B2 | 12/2009 | Rethy et al. |
| 7,637,409 B2 | 12/2009 | Marczyk |
| 7,641,092 B2 | 1/2010 | Kruszynski et al. |
| 7,641,093 B2 | 1/2010 | Doll et al. |
| 7,644,848 B2 * | 1/2010 | Swayze ............ A61B 17/07207 227/175.2 |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,699,204 B2 | 4/2010 | Viola |
| 7,708,180 B2 | 5/2010 | Murray et al. |
| 7,717,312 B2 | 5/2010 | Beetel |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shelton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,748,587 B2 | 7/2010 | Haramiishi et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,780,054 B2 | 8/2010 | Wales |
| 7,780,055 B2 | 8/2010 | Scirica et al. |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,080 B2 | 11/2010 | Schwemberger |
| 7,837,081 B2 | 11/2010 | Holsten et al. |
| 7,845,533 B2 | 12/2010 | Marczyk et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,221 B2 | 3/2011 | Viola et al. |
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,934,630 B2 | 5/2011 | Shelton, IV et al. |
| 7,938,307 B2 | 5/2011 | Bettuchi |
| 7,942,303 B2 | 5/2011 | Shah |
| 7,950,560 B2 | 5/2011 | Zemlok et al. |
| 7,951,071 B2 * | 5/2011 | Whitman ............ A61B 10/0233 600/101 |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,050 B2 | 6/2011 | Smith et al. |
| 7,959,051 B2 | 6/2011 | Smith et al. |
| 7,966,799 B2 | 6/2011 | Morgan et al. |
| 7,967,180 B2 | 6/2011 | Scirica |
| 7,980,443 B2 | 7/2011 | Scheib et al. |
| 8,011,551 B2 | 9/2011 | Marczyk et al. |
| 8,011,555 B2 | 9/2011 | Tarinelli et al. |
| 8,020,742 B2 | 9/2011 | Marczyk |
| 8,020,743 B2 | 9/2011 | Shelton, IV |
| 8,028,883 B2 | 10/2011 | Stopek |
| 8,038,045 B2 | 10/2011 | Bettuchi et al. |
| 8,056,787 B2 | 11/2011 | Boudreaux et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 8,091,756 B2 | 1/2012 | Viola |
| 8,113,410 B2 | 2/2012 | Hall et al. |
| 8,123,103 B2 | 2/2012 | Milliman |
| 8,136,712 B2 | 3/2012 | Zingman |
| 8,141,762 B2 | 3/2012 | Bedi et al. |
| 8,152,041 B2 | 4/2012 | Kostrzewski |
| 8,157,145 B2 * | 4/2012 | Shelton, IV ..... A61B 17/07207 227/175.1 |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,167,185 B2 | 5/2012 | Shelton, IV et al. |
| 8,172,124 B2 | 5/2012 | Shelton, IV et al. |
| 8,186,555 B2 | 5/2012 | Shelton, IV et al. |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,781 B2 | 6/2012 | Baxter, III et al. |
| 8,215,531 B2 | 7/2012 | Shelton, IV et al. |
| 8,220,688 B2 | 7/2012 | Laurent et al. |
| 8,220,690 B2 | 7/2012 | Hess et al. |
| 8,245,898 B2 | 8/2012 | Smith et al. |
| 8,245,901 B2 | 8/2012 | Stopek |
| 8,256,654 B2 | 9/2012 | Bettuchi et al. |
| 8,267,300 B2 | 9/2012 | Boudreaux |
| 8,292,155 B2 | 10/2012 | Shelton, IV et al. |
| 8,308,040 B2 | 11/2012 | Huang et al. |
| 8,317,070 B2 | 11/2012 | Hueil et al. |
| 8,322,455 B2 | 12/2012 | Shelton, IV et al. |
| 8,322,589 B2 | 12/2012 | Boudreaux |
| 8,333,313 B2 | 12/2012 | Boudreaux et al. |
| 8,348,129 B2 | 1/2013 | Bedi et al. |
| 8,348,131 B2 | 1/2013 | Omaits et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,360,296 B2 | 1/2013 | Zingman |

(56) References Cited

U.S. PATENT DOCUMENTS

| | | | |
|---|---|---|---|
| 8,360,297 B2 | 1/2013 | Shelton, IV et al. | |
| 8,365,976 B2 | 2/2013 | Hess et al. | |
| 8,371,393 B2* | 2/2013 | Higuchi | B27F 7/36 173/1 |
| 8,371,491 B2 | 2/2013 | Huitema et al. | |
| 8,453,914 B2 | 6/2013 | Laurent et al. | |
| 8,960,520 B2* | 2/2015 | McCuen | A61B 17/07207 227/175.1 |
| 8,967,443 B2* | 3/2015 | McCuen | A61B 17/07207 227/175.1 |
| 2002/0117534 A1 | 8/2002 | Green et al. | |
| 2002/0134811 A1 | 9/2002 | Napier et al. | |
| 2003/0130677 A1* | 7/2003 | Whitman | A61B 17/072 606/167 |
| 2004/0094597 A1 | 5/2004 | Whitman et al. | |
| 2004/0108357 A1 | 6/2004 | Milliman et al. | |
| 2004/0164123 A1 | 8/2004 | Racenet et al. | |
| 2004/0173659 A1 | 9/2004 | Green et al. | |
| 2004/0222268 A1 | 11/2004 | Bilotti et al. | |
| 2004/0232201 A1 | 11/2004 | Wenchell et al. | |
| 2005/0103819 A1 | 5/2005 | Racenet et al. | |
| 2005/0145675 A1 | 7/2005 | Hartwick et al. | |
| 2005/0184121 A1 | 8/2005 | Heinrich | |
| 2005/0189397 A1 | 9/2005 | Jankowski | |
| 2005/0263563 A1 | 12/2005 | Racenet et al. | |
| 2005/0274768 A1 | 12/2005 | Cummins et al. | |
| 2006/0011699 A1 | 1/2006 | Olson et al. | |
| 2006/0022015 A1* | 2/2006 | Shelton, IV | A61B 17/07207 227/176.1 |
| 2006/0049229 A1 | 3/2006 | Milliman et al. | |
| 2006/0060630 A1 | 3/2006 | Shelton, IV et al. | |
| 2006/0108393 A1 | 5/2006 | Heinrich et al. | |
| 2006/0180634 A1 | 8/2006 | Shelton, IV et al. | |
| 2006/0226196 A1 | 10/2006 | Hueil et al. | |
| 2006/0278680 A1* | 12/2006 | Viola | A61B 17/07207 227/176.1 |
| 2006/0278681 A1 | 12/2006 | Viola et al. | |
| 2006/0289602 A1 | 12/2006 | Wales et al. | |
| 2007/0023476 A1 | 2/2007 | Whitman et al. | |
| 2007/0023477 A1 | 2/2007 | Whitman et al. | |
| 2007/0034668 A1 | 2/2007 | Holsten et al. | |
| 2007/0084897 A1 | 4/2007 | Shelton, IV et al. | |
| 2007/0102472 A1 | 5/2007 | Shelton, IV | |
| 2007/0106317 A1 | 5/2007 | Shelton, IV et al. | |
| 2007/0114261 A1 | 5/2007 | Ortiz et al. | |
| 2007/0170225 A1 | 7/2007 | Shelton, IV et al. | |
| 2007/0175949 A1 | 8/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175955 A1 | 8/2007 | Shelton, IV et al. | |
| 2007/0175956 A1* | 8/2007 | Swayze | A61B 17/07207 227/178.1 |
| 2007/0181632 A1 | 8/2007 | Milliman | |
| 2007/0194079 A1 | 8/2007 | Hueil et al. | |
| 2007/0194082 A1 | 8/2007 | Morgan et al. | |
| 2007/0221700 A1 | 9/2007 | Ortiz et al. | |
| 2007/0221701 A1 | 9/2007 | Ortiz et al. | |
| 2007/0225562 A1 | 9/2007 | Spivey et al. | |
| 2007/0239028 A1 | 10/2007 | Houser et al. | |
| 2007/0246505 A1 | 10/2007 | Pace-Floridia et al. | |
| 2007/0270790 A1* | 11/2007 | Smith | A61B 17/115 606/32 |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0035701 A1 | 2/2008 | Racenet et al. | |
| 2008/0041916 A1 | 2/2008 | Milliman et al. | |
| 2008/0041917 A1 | 2/2008 | Racenet et al. | |
| 2008/0078800 A1 | 4/2008 | Hess et al. | |
| 2008/0078802 A1 | 4/2008 | Hess et al. | |
| 2008/0078803 A1 | 4/2008 | Shelton et al. | |
| 2008/0082125 A1 | 4/2008 | Murray et al. | |
| 2008/0082126 A1 | 4/2008 | Murray et al. | |
| 2008/0083813 A1 | 4/2008 | Zemlok et al. | |
| 2008/0167522 A1 | 7/2008 | Giordano et al. | |
| 2008/0167672 A1 | 7/2008 | Giordano et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0185419 A1 | 8/2008 | Smith et al. | |
| 2008/0197167 A1 | 8/2008 | Viola et al. | |
| 2008/0245841 A1 | 10/2008 | Smith et al. | |
| 2008/0251568 A1 | 10/2008 | Zemlok et al. | |
| 2008/0251569 A1 | 10/2008 | Smith et al. | |
| 2008/0283570 A1 | 11/2008 | Boyden et al. | |
| 2008/0290134 A1 | 11/2008 | Bettuchi et al. | |
| 2008/0296346 A1 | 12/2008 | Shelton, IV et al. | |
| 2008/0308602 A1 | 12/2008 | Timm et al. | |
| 2008/0308603 A1 | 12/2008 | Shelton, IV et al. | |
| 2008/0308608 A1 | 12/2008 | Prommersberger | |
| 2008/0314960 A1 | 12/2008 | Marczyk et al. | |
| 2009/0001121 A1 | 1/2009 | Hess et al. | |
| 2009/0001122 A1 | 1/2009 | Prommersberger et al. | |
| 2009/0001124 A1 | 1/2009 | Hess et al. | |
| 2009/0001130 A1 | 1/2009 | Hess et al. | |
| 2009/0005807 A1 | 1/2009 | Hess et al. | |
| 2009/0005808 A1 | 1/2009 | Hess et al. | |
| 2009/0005809 A1 | 1/2009 | Hess et al. | |
| 2009/0012556 A1 | 1/2009 | Boudreaux et al. | |
| 2009/0057369 A1 | 3/2009 | Smith et al. | |
| 2009/0090763 A1* | 4/2009 | Zemlok | A61B 17/07207 227/175.2 |
| 2009/0108048 A1 | 4/2009 | Zemlok et al. | |
| 2009/0114701 A1 | 5/2009 | Zemlok et al. | |
| 2009/0149871 A9 | 6/2009 | Kagan et al. | |
| 2009/0206125 A1 | 8/2009 | Huitema et al. | |
| 2009/0206126 A1 | 8/2009 | Huitema et al. | |
| 2009/0206131 A1 | 8/2009 | Weisenburgh, II et al. | |
| 2009/0206132 A1 | 8/2009 | Hueil et al. | |
| 2009/0206133 A1 | 8/2009 | Morgan et al. | |
| 2009/0206137 A1 | 8/2009 | Hall et al. | |
| 2009/0206139 A1 | 8/2009 | Hall et al. | |
| 2009/0206141 A1 | 8/2009 | Huitema et al. | |
| 2009/0206142 A1 | 8/2009 | Huitema et al. | |
| 2009/0209946 A1 | 8/2009 | Swayze et al. | |
| 2009/0209990 A1 | 8/2009 | Yates et al. | |
| 2009/0218384 A1 | 9/2009 | Aranyi | |
| 2009/0242610 A1 | 10/2009 | Shelton, IV et al. | |
| 2009/0255974 A1 | 10/2009 | Viola | |
| 2009/0255975 A1 | 10/2009 | Zemlok et al. | |
| 2009/0255976 A1 | 10/2009 | Marczyk et al. | |
| 2009/0255977 A1 | 10/2009 | Zemlok | |
| 2009/0255978 A1 | 10/2009 | Viola et al. | |
| 2009/0308907 A1 | 12/2009 | Nalagatla et al. | |
| 2010/0012704 A1 | 1/2010 | Tarinelli Racenet et al. | |
| 2010/0069942 A1 | 3/2010 | Shelton, IV | |
| 2010/0072254 A1 | 3/2010 | Aranyi et al. | |
| 2010/0076474 A1* | 3/2010 | Yates | A61B 17/07207 606/170 |
| 2010/0076475 A1 | 3/2010 | Yates et al. | |
| 2010/0089970 A1 | 4/2010 | Smith et al. | |
| 2010/0089972 A1 | 4/2010 | Marczyk | |
| 2010/0096431 A1* | 4/2010 | Smith | A61B 17/00 227/175.2 |
| 2010/0108740 A1 | 5/2010 | Pastorelli et al. | |
| 2010/0108741 A1 | 5/2010 | Hessler et al. | |
| 2010/0127042 A1 | 5/2010 | Shelton, IV | |
| 2010/0133317 A1 | 6/2010 | Shelton, IV et al. | |
| 2010/0163598 A1 | 7/2010 | Belzer | |
| 2010/0179382 A1 | 7/2010 | Shelton, IV et al. | |
| 2010/0193566 A1 | 8/2010 | Scheib et al. | |
| 2010/0193567 A1 | 8/2010 | Scheib et al. | |
| 2010/0193568 A1 | 8/2010 | Scheib et al. | |
| 2010/0193569 A1 | 8/2010 | Yates et al. | |
| 2010/0198220 A1 | 8/2010 | Boudreaux et al. | |
| 2010/0200637 A1 | 8/2010 | Beetel | |
| 2010/0211053 A1* | 8/2010 | Ross | A61B 17/068 606/1 |
| 2010/0213241 A1 | 8/2010 | Bedi et al. | |

(56) References Cited

U.S. PATENT DOCUMENTS

| | | | |
|---|---|---|---|
| 2010/0222901 A1 | 9/2010 | Swayze et al. | |
| 2010/0224669 A1 | 9/2010 | Shelton, IV et al. | |
| 2010/0230465 A1 | 9/2010 | Smith et al. | |
| 2010/0243707 A1 | 9/2010 | Olson et al. | |
| 2010/0243708 A1 | 9/2010 | Aranyi et al. | |
| 2010/0243709 A1 | 9/2010 | Hess et al. | |
| 2010/0258611 A1 | 10/2010 | Smith et al. | |
| 2010/0264193 A1 | 10/2010 | Huang et al. | |
| 2010/0270355 A1* | 10/2010 | Whitman | A61B 17/068 227/176.1 |
| 2010/0276471 A1 | 11/2010 | Whitman | |
| 2010/0294827 A1 | 11/2010 | Boyden et al. | |
| 2010/0294829 A1 | 11/2010 | Giordano et al. | |
| 2010/0301095 A1 | 12/2010 | Shelton, IV et al. | |
| 2010/0305552 A1 | 12/2010 | Shelton, IV et al. | |
| 2011/0006099 A1 | 1/2011 | Hall et al. | |
| 2011/0006101 A1 | 1/2011 | Hall et al. | |
| 2011/0006103 A1 | 1/2011 | Laurent et al. | |
| 2011/0011914 A1 | 1/2011 | Baxter, III et al. | |
| 2011/0011915 A1 | 1/2011 | Shelton, IV | |
| 2011/0017801 A1 | 1/2011 | Zemlok et al. | |
| 2011/0022032 A1 | 1/2011 | Zemlok et al. | |
| 2011/0024477 A1 | 2/2011 | Hall et al. | |
| 2011/0024478 A1 | 2/2011 | Shelton, IV | |
| 2011/0024479 A1 | 2/2011 | Swensgard et al. | |
| 2011/0036887 A1 | 2/2011 | Zemlok et al. | |
| 2011/0042441 A1 | 2/2011 | Shelton, IV et al. | |
| 2011/0060363 A1 | 3/2011 | Hess et al. | |
| 2011/0068145 A1 | 3/2011 | Bedi et al. | |
| 2011/0068148 A1 | 3/2011 | Hall et al. | |
| 2011/0084112 A1 | 4/2011 | Kostrzewski | |
| 2011/0087276 A1 | 4/2011 | Bedi et al. | |
| 2011/0095068 A1 | 4/2011 | Patel | |
| 2011/0101065 A1 | 5/2011 | Milliman | |
| 2011/0114697 A1 | 5/2011 | Baxter, III et al. | |
| 2011/0114700 A1 | 5/2011 | Baxter, III et al. | |
| 2011/0118761 A1 | 5/2011 | Baxter, III et al. | |
| 2011/0125176 A1 | 5/2011 | Yates et al. | |
| 2011/0125177 A1 | 5/2011 | Yates et al. | |
| 2011/0132963 A1 | 6/2011 | Giordano et al. | |
| 2011/0132964 A1 | 6/2011 | Weisenburgh, II et al. | |
| 2011/0132965 A1 | 6/2011 | Moore et al. | |
| 2011/0144430 A1 | 6/2011 | Spivey et al. | |
| 2011/0147433 A1 | 6/2011 | Shelton, IV et al. | |
| 2011/0147434 A1 | 6/2011 | Hueil et al. | |
| 2011/0155781 A1 | 6/2011 | Swensgard et al. | |
| 2011/0155787 A1 | 6/2011 | Baxter, III et al. | |
| 2011/0163147 A1 | 7/2011 | Laurent et al. | |
| 2011/0174861 A1 | 7/2011 | Shelton, IV et al. | |
| 2011/0174863 A1 | 7/2011 | Shelton, IV et al. | |
| 2011/0192882 A1 | 8/2011 | Hess et al. | |
| 2011/0204119 A1* | 8/2011 | McCuen | A61B 17/07207 227/175.1 |
| 2011/0210156 A1 | 9/2011 | Smith et al. | |
| 2011/0226837 A1 | 9/2011 | Baxter, III et al. | |
| 2011/0275901 A1 | 11/2011 | Shelton, IV | |
| 2011/0276083 A1 | 11/2011 | Shelton, IV et al. | |
| 2011/0288573 A1 | 11/2011 | Yates et al. | |
| 2011/0290851 A1 | 12/2011 | Shelton, IV | |
| 2011/0290853 A1 | 12/2011 | Shelton, IV et al. | |
| 2011/0290854 A1 | 12/2011 | Timm et al. | |
| 2011/0290855 A1 | 12/2011 | Moore et al. | |
| 2011/0290856 A1 | 12/2011 | Shelton, IV et al. | |
| 2011/0295242 A1 | 12/2011 | Spivey et al. | |
| 2011/0295269 A1* | 12/2011 | Swensgard | A61B 17/068 606/130 |
| 2011/0295270 A1 | 12/2011 | Giordano et al. | |
| 2011/0295295 A1 | 12/2011 | Shelton, IV et al. | |
| 2012/0024934 A1 | 2/2012 | Shelton, IV et al. | |
| 2012/0024935 A1 | 2/2012 | Shelton, IV et al. | |
| 2012/0024936 A1 | 2/2012 | Baxter, III et al. | |
| 2012/0029272 A1 | 2/2012 | Shelton, IV et al. | |
| 2012/0029544 A1 | 2/2012 | Shelton, IV et al. | |
| 2012/0029547 A1 | 2/2012 | Shelton, IV et al. | |
| 2012/0071711 A1 | 3/2012 | Shelton, IV et al. | |
| 2012/0071866 A1 | 3/2012 | Kerr et al. | |
| 2012/0074196 A1 | 3/2012 | Shelton, IV et al. | |
| 2012/0074198 A1 | 3/2012 | Huitema et al. | |
| 2012/0074200 A1 | 3/2012 | Schmid et al. | |
| 2012/0074201 A1 | 3/2012 | Baxter, III et al. | |
| 2012/0080332 A1 | 4/2012 | Shelton, IV et al. | |
| 2012/0080333 A1 | 4/2012 | Woodard, Jr. et al. | |
| 2012/0080334 A1 | 4/2012 | Shelton, IV et al. | |
| 2012/0080335 A1 | 4/2012 | Shelton, IV et al. | |
| 2012/0080336 A1 | 4/2012 | Shelton, IV et al. | |
| 2012/0080337 A1 | 4/2012 | Shelton, IV et al. | |
| 2012/0080338 A1 | 4/2012 | Shelton, IV et al. | |
| 2012/0080339 A1 | 4/2012 | Shelton, IV et al. | |
| 2012/0080340 A1 | 4/2012 | Shelton, IV et al. | |
| 2012/0080344 A1 | 4/2012 | Shelton, IV | |
| 2012/0080345 A1 | 4/2012 | Morgan et al. | |
| 2012/0080475 A1 | 4/2012 | Smith et al. | |
| 2012/0080477 A1* | 4/2012 | Leimbach | A61B 17/07207 227/175.2 |
| 2012/0080478 A1 | 4/2012 | Morgan et al. | |
| 2012/0080479 A1 | 4/2012 | Shelton, IV | |
| 2012/0080480 A1 | 4/2012 | Woodard, Jr. et al. | |
| 2012/0080481 A1 | 4/2012 | Widenhouse et al. | |
| 2012/0080482 A1 | 4/2012 | Schall et al. | |
| 2012/0080483 A1 | 4/2012 | Riestenberg et al. | |
| 2012/0080484 A1 | 4/2012 | Morgan et al. | |
| 2012/0080485 A1 | 4/2012 | Woodard, Jr. et al. | |
| 2012/0080486 A1 | 4/2012 | Woodard, Jr. et al. | |
| 2012/0080487 A1 | 4/2012 | Woodard, Jr. et al. | |
| 2012/0080488 A1 | 4/2012 | Shelton, IV et al. | |
| 2012/0080489 A1 | 4/2012 | Shelton, IV et al. | |
| 2012/0080490 A1 | 4/2012 | Shelton, IV et al. | |
| 2012/0080491 A1 | 4/2012 | Shelton, IV et al. | |
| 2012/0080493 A1 | 4/2012 | Shelton, IV et al. | |
| 2012/0080496 A1 | 4/2012 | Schall et al. | |
| 2012/0080498 A1 | 4/2012 | Shelton, IV et al. | |
| 2012/0080499 A1 | 4/2012 | Schall et al. | |
| 2012/0080500 A1 | 4/2012 | Morgan et al. | |
| 2012/0080501 A1 | 4/2012 | Morgan et al. | |
| 2012/0080502 A1 | 4/2012 | Morgan et al. | |
| 2012/0080503 A1 | 4/2012 | Woodard, Jr. et al. | |
| 2012/0083833 A1 | 4/2012 | Shelton, IV et al. | |
| 2012/0083834 A1 | 4/2012 | Shelton, IV et al. | |
| 2012/0083835 A1 | 4/2012 | Shelton, IV et al. | |
| 2012/0083836 A1 | 4/2012 | Shelton, IV et al. | |
| 2012/0132450 A1 | 5/2012 | Timm et al. | |
| 2012/0138658 A1* | 6/2012 | Ullrich | A61B 17/072 227/175.1 |
| 2012/0138660 A1 | 6/2012 | Shelton, IV | |
| 2012/0160721 A1 | 6/2012 | Shelton, IV et al. | |
| 2012/0175399 A1 | 7/2012 | Shelton et al. | |
| 2012/0187179 A1 | 7/2012 | Gleiman | |
| 2012/0199630 A1 | 8/2012 | Shelton, IV et al. | |
| 2012/0199631 A1 | 8/2012 | Shelton, IV et al. | |
| 2012/0199632 A1 | 8/2012 | Spivey et al. | |
| 2012/0199633 A1 | 8/2012 | Shelton, IV et al. | |
| 2012/0203247 A1 | 8/2012 | Shelton, IV et al. | |
| 2012/0205421 A1 | 8/2012 | Shelton, IV | |
| 2012/0211546 A1 | 8/2012 | Shelton, IV | |
| 2012/0234890 A1 | 9/2012 | Aronhalt et al. | |
| 2012/0234891 A1 | 9/2012 | Aronhalt et al. | |
| 2012/0234892 A1 | 9/2012 | Aronhalt et al. | |
| 2012/0234893 A1 | 9/2012 | Schuckmann et al. | |
| 2012/0234895 A1 | 9/2012 | O'Connor et al. | |
| 2012/0234896 A1 | 9/2012 | Ellerhorst et al. | |
| 2012/0234897 A1 | 9/2012 | Shelton, IV et al. | |
| 2012/0234898 A1 | 9/2012 | Shelton, IV et al. | |
| 2012/0234899 A1 | 9/2012 | Scheib et al. | |
| 2012/0234900 A1 | 9/2012 | Swayze | |
| 2012/0238823 A1 | 9/2012 | Hagerty et al. | |
| 2012/0238824 A1 | 9/2012 | Widenhouse et al. | |
| 2012/0238826 A1 | 9/2012 | Yoo et al. | |
| 2012/0238829 A1 | 9/2012 | Shelton, IV et al. | |
| 2012/0239009 A1 | 9/2012 | Mollere et al. | |
| 2012/0239010 A1 | 9/2012 | Shelton, IV et al. | |
| 2012/0239075 A1 | 9/2012 | Widenhouse et al. | |
| 2012/0239082 A1 | 9/2012 | Shelton, IV et al. | |
| 2012/0241491 A1 | 9/2012 | Aldridge et al. | |
| 2012/0241492 A1 | 9/2012 | Shelton, IV et al. | |

(56) References Cited

U.S. PATENT DOCUMENTS

| | | |
|---|---|---|
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, IV et al. |
| 2012/0283707 A1 | 11/2012 | Giordano et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2013/0012931 A1 | 1/2013 | Spivey et al. |
| 2013/0012957 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0041371 A1 | 2/2013 | Yates et al. |

FOREIGN PATENT DOCUMENTS

| | | |
|---|---|---|
| CA | 2514274 A1 | 1/2006 |
| CN | 1634601 A | 7/2005 |
| CN | 1868411 A | 11/2006 |
| CN | 1915180 A | 2/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 B1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |

(56) References Cited

FOREIGN PATENT DOCUMENTS

| | | |
|---|---|---|
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1632191 A2 | 3/2006 |
| EP | 1065981 B1 | 5/2006 |
| EP | 1082944 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1487359 B1 | 10/2007 |
| EP | 1599146 B1 | 10/2007 |
| EP | 1839596 B1 | 10/2007 |
| EP | 2110083 A2 | 10/2007 |
| EP | 1857057 A2 | 11/2007 |
| EP | 1402821 B1 | 12/2007 |
| EP | 1872727 A1 | 1/2008 |
| EP | 1897502 A1 | 3/2008 |
| EP | 1330201 B1 | 6/2008 |
| EP | 1702568 B1 | 7/2008 |
| EP | 1943957 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1990014 A2 | 11/2008 |
| EP | 1693008 B1 | 12/2008 |
| EP | 1759640 B1 | 12/2008 |
| EP | 2000102 A2 | 12/2008 |
| EP | 2008595 A2 | 12/2008 |
| EP | 1736104 B1 | 3/2009 |
| EP | 1749486 B1 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 1550413 B1 | 6/2009 |
| EP | 1745748 B1 | 8/2009 |
| EP | 2090237 A1 | 8/2009 |
| EP | 2090244 A2 | 8/2009 |
| EP | 2090256 A2 | 8/2009 |
| EP | 2095777 A2 | 9/2009 |
| EP | 2110082 A1 | 10/2009 |
| EP | 1813208 B1 | 11/2009 |
| EP | 2116195 A1 | 11/2009 |
| EP | 1607050 B1 | 12/2009 |
| EP | 1815804 B1 | 12/2009 |
| EP | 1566150 B1 | 4/2010 |
| EP | 1813206 B1 | 4/2010 |
| EP | 1769754 B1 | 6/2010 |
| EP | 1535565 B1 | 10/2010 |
| EP | 1702570 B1 | 10/2010 |
| EP | 1785098 B1 | 10/2010 |
| EP | 2030578 B1 | 11/2010 |
| EP | 1627605 B1 | 12/2010 |
| EP | 1813205 B1 | 6/2011 |
| EP | 1785102 B1 | 1/2012 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | S 58500053 A | 1/1983 |
| JP | 61-98249 A | 5/1986 |
| JP | 63-203149 A | 8/1988 |
| JP | 3-12126 A | 1/1991 |
| JP | 5-212039 A | 8/1993 |
| JP | 6007357 A | 1/1994 |
| JP | 7051273 A | 2/1995 |
| JP | 8033641 A | 2/1996 |
| JP | 8229050 A | 9/1996 |
| JP | 2000033071 A | 2/2000 |
| JP | 2000171730 A | 6/2000 |
| JP | 2000287987 A | 10/2000 |
| JP | 2000325303 A | 11/2000 |

(56) References Cited

FOREIGN PATENT DOCUMENTS

| | | |
|---|---|---|
| JP | 2001-514541 A | 9/2001 |
| JP | 2001286477 A | 10/2001 |
| JP | 2002143078 A | 5/2002 |
| JP | 2002369820 A | 12/2002 |
| JP | 2004-344663 A | 12/2004 |
| JP | 2005-028149 A | 2/2005 |
| JP | 2005505322 T | 2/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2006-281405 A | 10/2006 |
| RU | 2008830 C1 | 3/1994 |
| RU | 2187249 C2 | 8/2002 |
| RU | 2225170 C2 | 3/2004 |
| SU | 189517 A | 1/1967 |
| SU | 328636 A | 9/1972 |
| SU | 886900 A1 | 12/1981 |
| SU | 1009439 A | 4/1983 |
| SU | 1333319 A2 | 8/1987 |
| SU | 1377053 A1 | 2/1988 |
| SU | 1561964 A1 | 5/1990 |
| SU | 1722476 A1 | 3/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |

(56) References Cited

FOREIGN PATENT DOCUMENTS

| | | |
|---|---|---|
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/109125 A1 | 9/2008 |
| WO | WO 2010/063795 A1 | 6/2010 |
| WO | WO 2012/044844 A2 | 4/2012 |

OTHER PUBLICATIONS

U.S. Appl. No. 12/031,573, filed Feb. 14, 2008.
U.S. Appl. No. 12/693,462, filed Jan. 26, 2010.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 a Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).

\* cited by examiner

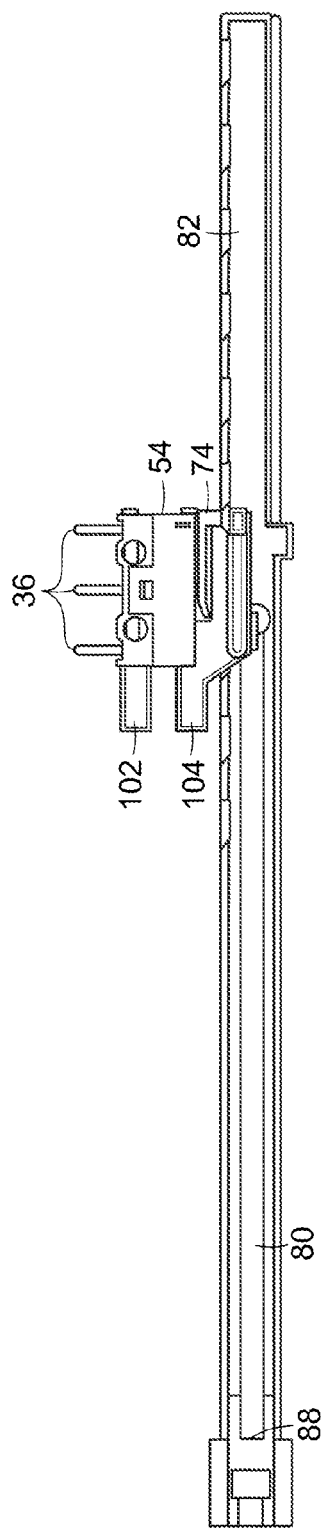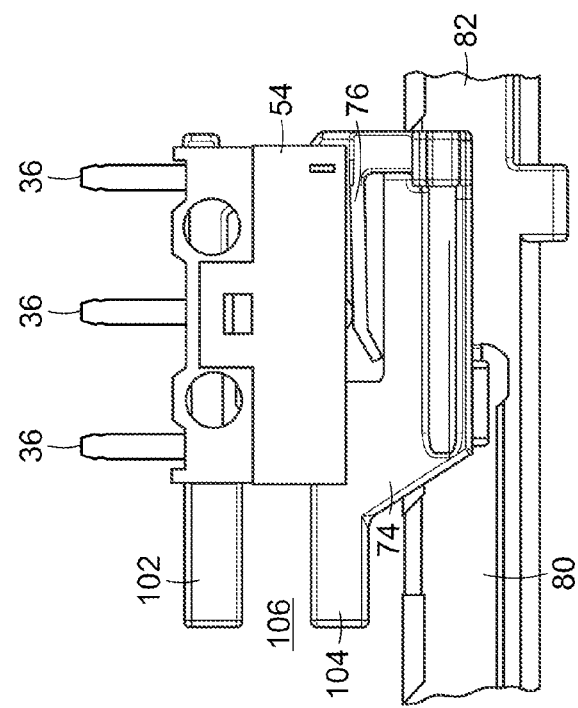

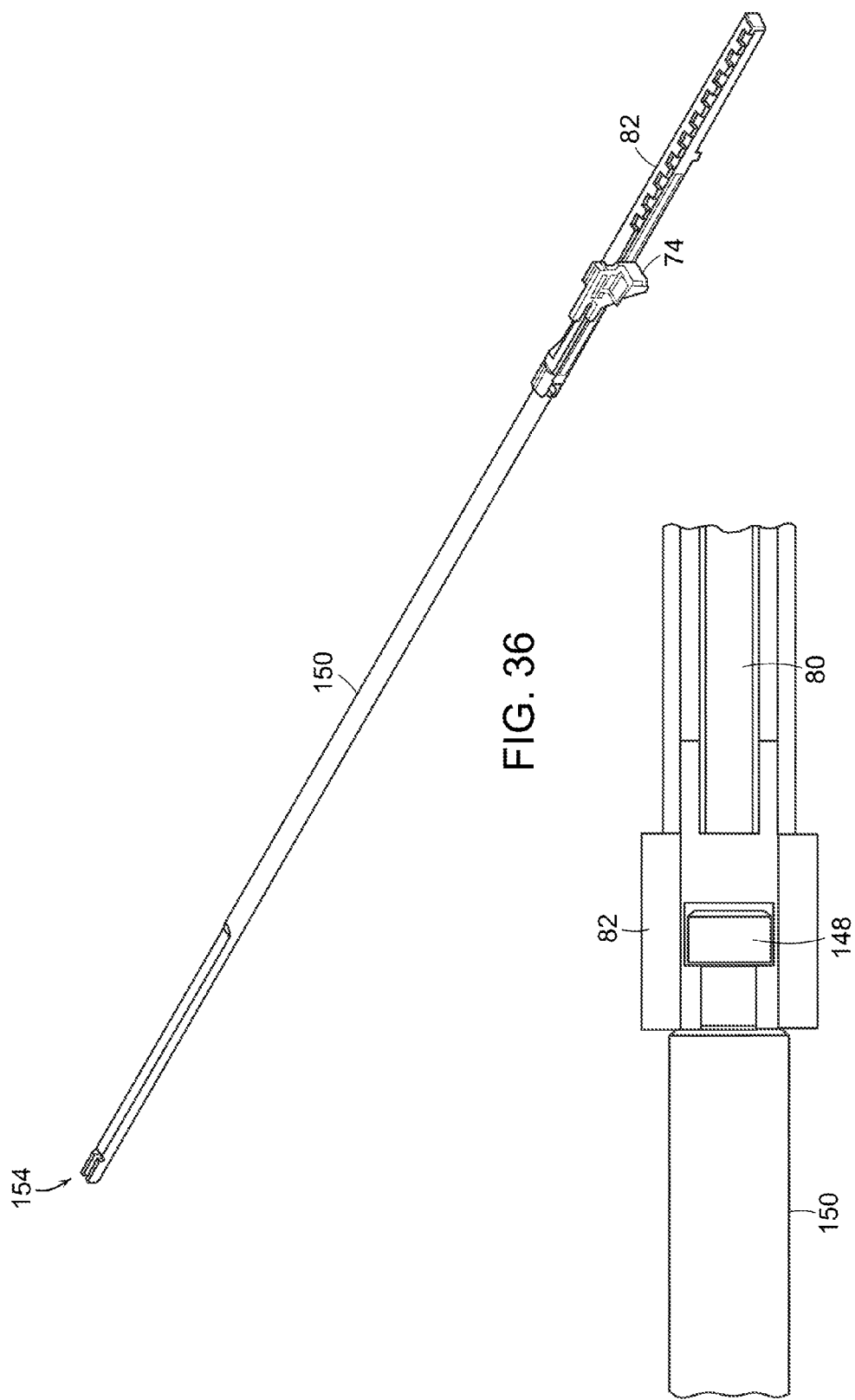

MOTOR-DRIVEN SURGICAL CUTTING INSTRUMENT WITH ELECTRIC ACTUATOR DIRECTIONAL CONTROL ASSEMBLY

PRIORITY CLAIM

This application claims priority as a continuation to U.S. patent application Ser. No. 13/482,179, entitled "MOTOR-DRIVEN SURGICAL CUTTING INSTRUMENT WITH ELECTRIC ACTUATOR DIRECTIONAL CONTROL ASSEMBLY," filed May 29, 2012, to be issued as U.S. Pat. No. 8,453,914 on Jun. 4, 2013, which is a continuation of U.S. patent application Ser. No. 12/647,100, entitled "MOTOR-DRIVEN SURGICAL CUTTING INSTRUMENT WITH ELECTRIC ACTUATOR DIRECTIONAL CONTROL ASSEMBLY," filed Dec. 24, 2009, now U.S. Pat. No. 8,220,688 issued on Jun. 17, 2012, both of which are incorporated herein by reference in their entirety.

BACKGROUND

Surgical staplers are used to simultaneously make a longitudinal incision in tissue and apply lines of staples on opposing sides of the incision. Such instruments commonly include an end effector having a pair of cooperating jaw members that, if the instrument is intended for endoscopic or laparoscopic applications, are capable of passing through a cannula passageway. One of the jaw members receives a staple cartridge having at least two laterally spaced rows of staples—one on each side of the knife channel. The other jaw member defines an anvil having staple-forming pockets aligned with the rows of staples in the cartridge. The instrument includes a plurality of reciprocating wedges that, when driven distally, pass through openings in the staple cartridge and engage drivers supporting the staples to effect the firing of the staples toward the anvil. Simultaneously, a cutting instrument (or knife) is drawn distally along the jaw member so that the clamped tissue is cut and fastened (e.g., stapled) at the same time.

An example of a surgical stapler suitable for endoscopic applications is described in published U.S. patent application Pub. No. 2004/0232196 A1, entitled, "Surgical stapling instrument having separate distinct closing and firing systems," the disclosure of which is herein incorporated by reference in its entirety. In use, a clinician is able to close the jaw members of the stapler upon tissue to position the tissue prior to firing. Once the clinician has determined that the jaw members are properly gripping tissue, the clinician can then fire the surgical stapler, thereby severing and stapling the tissue. The simultaneous severing and stapling actions avoid complications that may arise when performing such actions sequentially with different surgical tools that respectively only sever or staple.

Motor-driven endocutters are known in the art. In such devices, an electric motor powers the cutting and fastening action of the instrument. It is also known to use an on-board battery, located in the handle of the instrument, to power the motor. Published U.S. Patent Application Publication No. 2007/0175952 A1, entitled "Motor-driven surgical cutting and fastening instrument with loading force feedback," the disclosure of which is herein incorporated by reference in its entirety, describes one such motor-driven surgical instrument.

In motor-driven surgical instruments, it is sometimes preferable that the control circuit for controlling the operation of the motor does not include any integrated circuits (ICs) made of semiconductor material because it is often difficult, complicated, and expensive to sterilize a surgical instrument including ICs.

SUMMARY

In one general aspect, the present invention is directed to a motor-driven surgical instrument having a control assembly for controlling a switch of the instrument. The switch may be part of the circuit that controls the motor or part of some other circuit in the instrument. In various embodiments, the surgical instrument comprises: (i) a handle; (ii) an end effector connected to the handle; (iii) an electric motor in the handle for powering the end effector; (iv) a motor control circuit connected to the motor for controlling the motor; (v) a drive member that is driven by the motor; and (vi) a slider. The motor control circuit comprises a plurality of switches, including a first switch with a moveable (e.g., depressible) actuator (e.g., plunger). The drive member, when driven by the motor, causes movement of a moveable component of the end effector, and the drive member comprises a first shoulder at a first position and a second shoulder at a second position. The slider comprises a first portion and a second portion. The first portion interfaces the drive member such that the slider is moveable in a direction of movement of the drive member when either the first shoulder or the second shoulder of the drive member engages the first portion of the slider. The second portion of the slider actuates the moveable actuator of the first switch when the drive member moves the slider to a first position relative to the first switch. In various embodiments, the switches of the control circuit are not embodied as a part of an IC. Thus in various embodiments, the motor control circuit does not comprise an integrated circuit. In various embodiments, the first switch controls the direction of rotation of the motor.

In various embodiments, the drive member may move longitudinally or rotationally when actuated by the motor. For example, in one embodiment, the drive member comprises a longitudinally moveable rack that has, on one side, teeth geared to a pinion that is rotated by the motor, and that defines a channel having the first and second shoulders on the other side of the rack. The first portion of the slider that interfaces with the drive member may comprises one or more tabs that extend into the channel. The second portion of the slider that actuates the switch may comprise a cantilevered arm.

In yet another general aspect, the motor control circuit comprises a switching circuit that, upon actuation, reverses the direction of the motor, and is actuatable separately through each of: (i) actuation of a moveable actuator of the switching circuit through movement of the drive member at least in the first direction; and (ii) manual actuation by a user of the surgical instrument.

FIGURES

Various embodiments of the present invention are described herein by way of example in connection with the following figures, wherein:

FIGS. 20-21 is front side views of the direction control switch, the slider, and the rack according to various embodiments;

FIGS. 36-37 are diagrams that show the rack connected to the drive shaft according to various embodiments.

DESCRIPTION

Certain embodiments of the present invention will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of these embodiments is defined solely by the claims. The features illustrated or described in connection with one embodiment may be combined with the features of other embodiments. Such modifications and variations are intended to be included within the scope of the appended claims.

Figure 1:
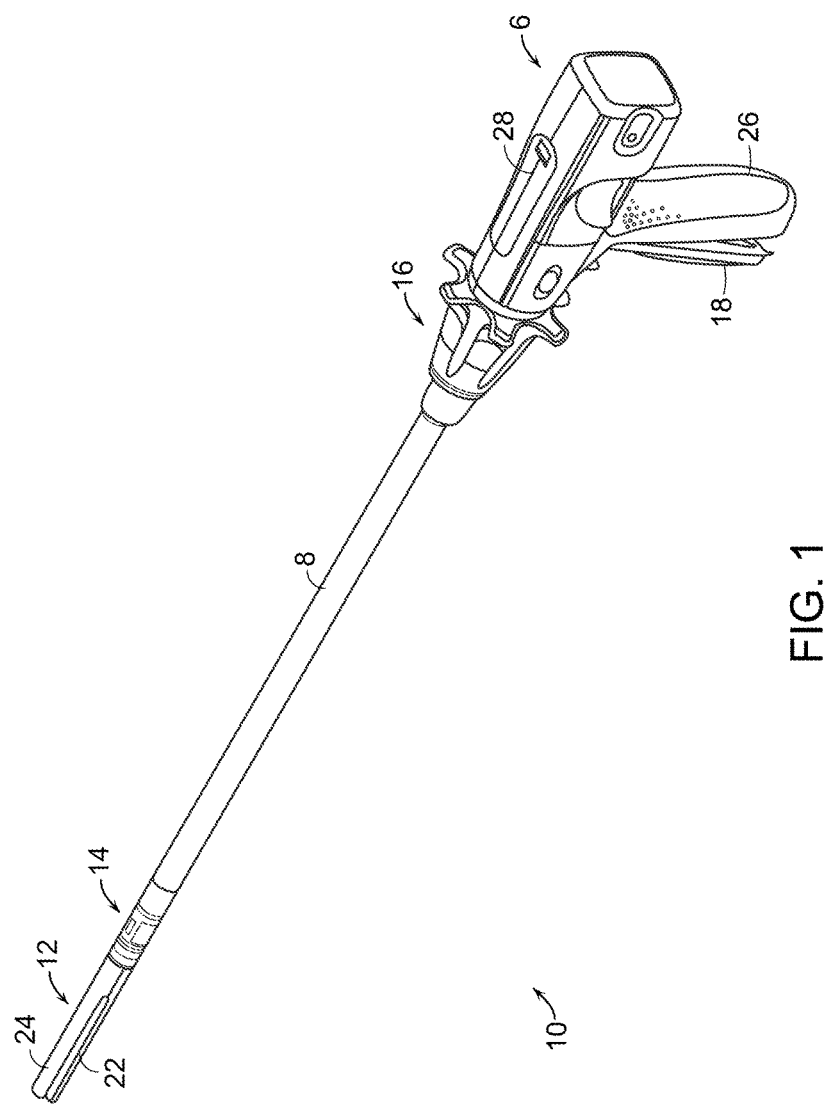
FIG. 1 is a perspective view of a surgical instrument 10 according to various embodiments of the present invention, showing the handle, shaft, and end effector.
Figure 2:
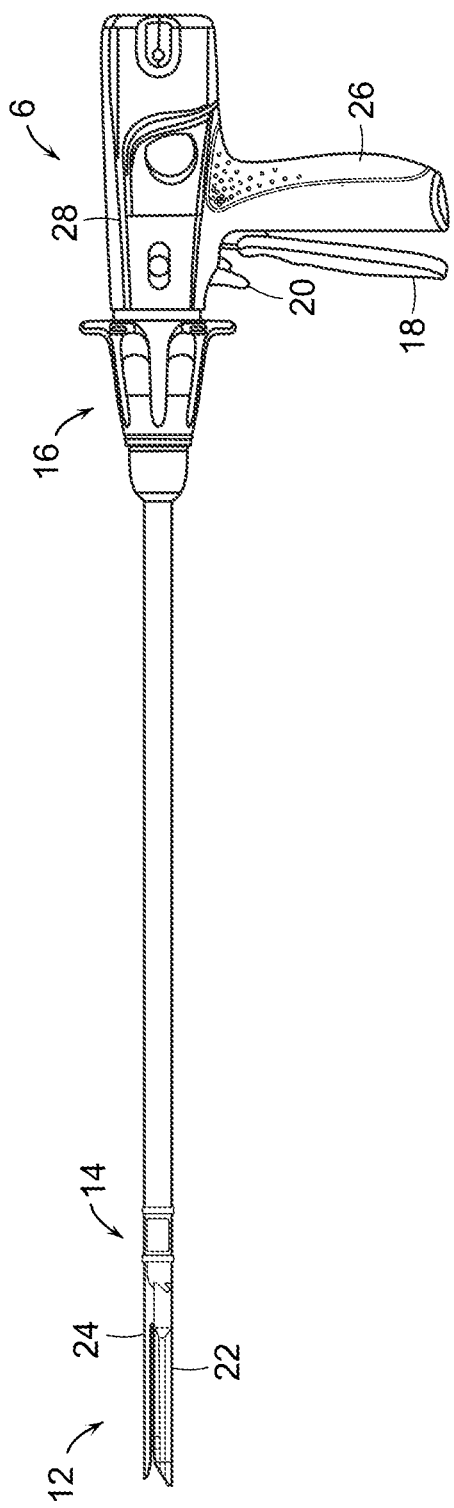
FIG. 2 is side view of a surgical instrument 10 according to various embodiments of the present invention, showing the handle, the shaft, and the end effector.

In general, embodiments of the present invention are directed to a motor-driven surgical instrument that comprises a mechanically actuated slider for actuating an electric switch of the motor control circuit that controls the operation of the electric motor. For example, actuation of the switch may reverse the polarity of the voltage supplied to the motor, to thereby reverse the rotation of the motor. FIGS. 1 and 2 depict a motor-driven surgical cutting and fastening instrument 10 that may include the mechanically actuated slider according to various embodiments of the present invention. The illustrated embodiment is an endoscopic instrument and, in general, the embodiments of the instrument 10 described herein are endoscopic surgical cutting and fastening instruments. It should be noted, however, that the invention is not so limited and that according to other embodiments of the present invention, the instrument may be a non-endoscopic surgical cutting and fastening instrument, such as a laparoscopic instrument.

The surgical instrument 10 depicted in FIGS. 1 and 2 comprises a handle 6, a shaft 8, and an end effector 12 connected to the shaft 8. In various embodiments, the end effector 12 can be articulated about an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc. More details regarding RF devices may be found in U.S. Pat. No. 5,403,312 and U.S. patent application Ser. No. 12/031,573, entitled "Surgical cutting and fastening instrument having RF electrodes, filed Feb. 14, 2008, both of which are incorporated by reference in their entirety.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by the elongate shaft 8. In one embodiment, a clinician or operator of the instrument 10 may articulate the end effector 12 relative to the shaft 8 by utilizing the articulation control 16, as described in more detail in published U.S. Patent Application Publication No. 2007/0158385 A1, entitled "Surgical Instrument Having An Articulating End Effector," by Geoffrey C. Hueil et al., which is incorporated herein by reference in its entirety.

The end effector 12 includes in this example, among other things, a staple channel 22 and a pivotally translatable clamping member, such as an anvil 24, which are maintained at a spacing that assures, when the anvil 24 is in its clamped position, effective stapling and severing of tissue clamped in the end effector 12. The handle 6 includes a downwardly extending pistol grip 26, towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12. In other embodiments, different types of clamping members besides the anvil 24 could be used. The handle 6 may also include an upper portion 28 that may sit on top of the user's hand when the user grips the pistol grip portion 26 with his/her hand.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

In operational use, the closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure. A release button on the handle 6, when depressed may release the locked closure trigger 18. The release button may be implemented in various forms such as, for example, as disclosed in published U.S. Patent Application Publication No. 2007/0175955, entitled "Surgical cutting and fastening instrument with closure trigger locking mechanism," which is incorporated herein by reference in its entirety.

The end effector 12 may include a cutting instrument, such as knife, for cutting tissue clamped in the end effector 12 when the firing trigger 20 is retracted by a user. The end effector 12 may also comprise means for fastening the tissue severed by the cutting instrument, such as staples, RF electrodes, adhesives, etc. More details regarding possible configurations of the end effector 12 may be found in the following patents and published patent applications, which are incorporated herein by reference in their entirety: U.S. Pat. No. 5,709,680; U.S. Pat. No. 5,688,270; U.S. Pat. No. 7,000,818; U.S. Patent Publication No. 2005/0173490 A1; U.S. Patent Publication No. 2006/0025809 A1; U.S. Patent Publication No. 2007/0102453 A1; U.S. Patent Publication No. 2007/0102452 A1; U.S. Patent Publication No. 2009/0206134 A1; and U.S. Patent Publication No. 2009/0206124 A1.

The instrument 10 may also comprise a closure system for closing (or clamping) the end effector upon closure (or retraction) of the closure trigger 18. More details regarding embodiments of an exemplary closure system for closing (or clamping) the anvil 24 of the end effector 12 by retracting the closure trigger 18 are provided in the following U.S. Patent references, which are incorporated herein by reference in their entirety: U.S. Patent Publication No. 2004/0232196 A1; U.S. Patent Publication No. 2007/0175956 A1; U.S. Patent Publication No. 2007/0158385 A1; U.S. Patent Publication No. 2007/0175962 A1; U.S. Pat. No. 7,464,849; and the references cited in the paragraph above.

A longitudinally movable drive shaft located within the shaft 8 of the instrument 10 may drive/actuate the cutting instrument and the fastening means in the end effector 12. An electric motor, located in the pistol grip portion 26 of the handle 6 of the instrument 10, may be used to drive, indirectly, the drive shaft, as described further herein. In various embodiments, the motor may be a DC brushed driving motor having a maximum rotation of, approximately, 25,000 RPM. In other embodiments, the motor may include a brushless motor, a cordless motor, a synchronous motor, a stepper motor, or any other suitable electric motor. A battery (or "power source" or "power pack"), such as a Li ion battery, may be provided in the pistol grip portion 26 of the handle 6 adjacent to the motor. The battery supplies electric power to the motor via a motor control circuit. According to various embodiments, a number of battery cells connected in series may be used as the power source to power the motor. In addition, the power source may be replaceable and/or rechargeable.

Figure 3:
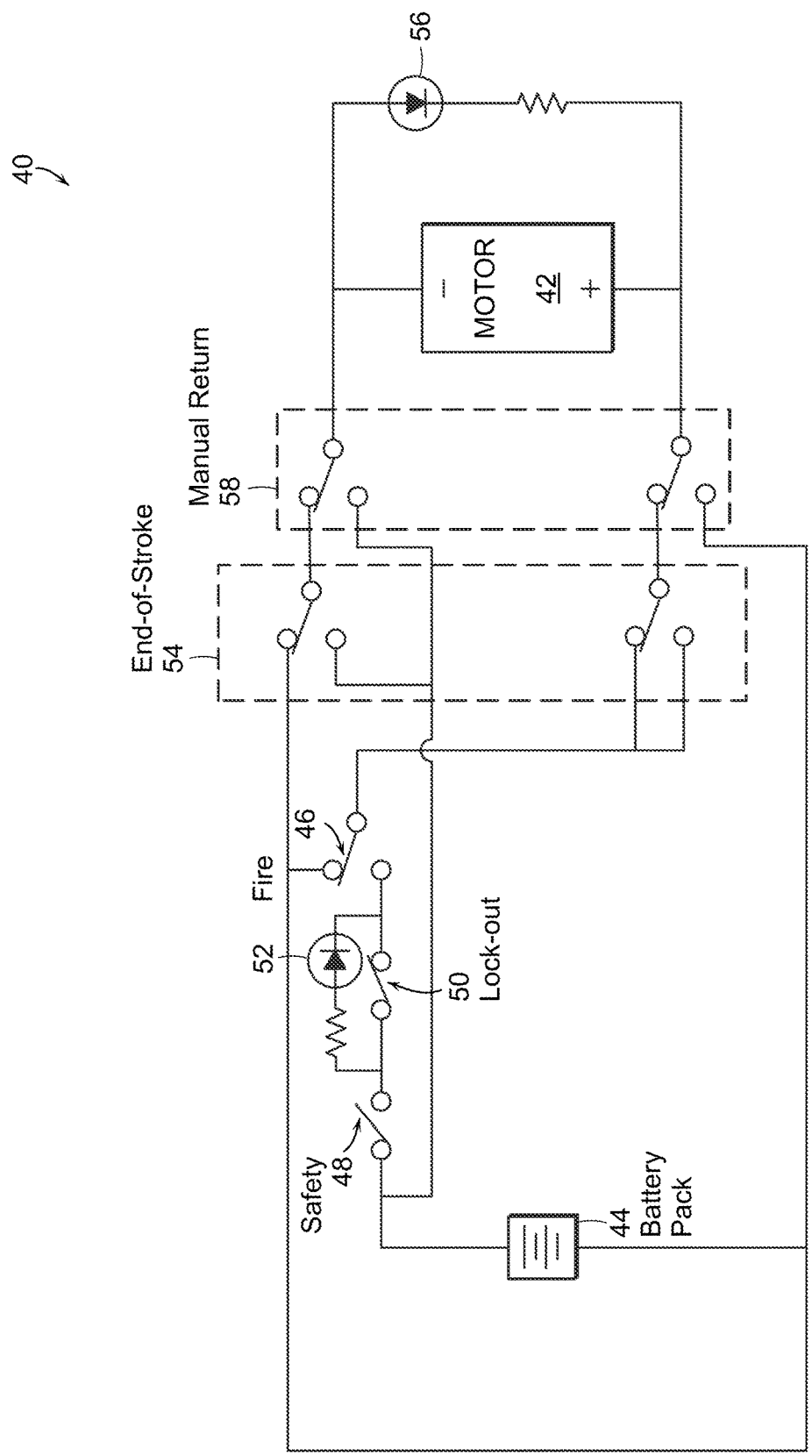
FIG. 3 is a schematic diagram of a motor control circuit for controlling the motor of the surgical instrument according to various embodiments.
Figure 4:
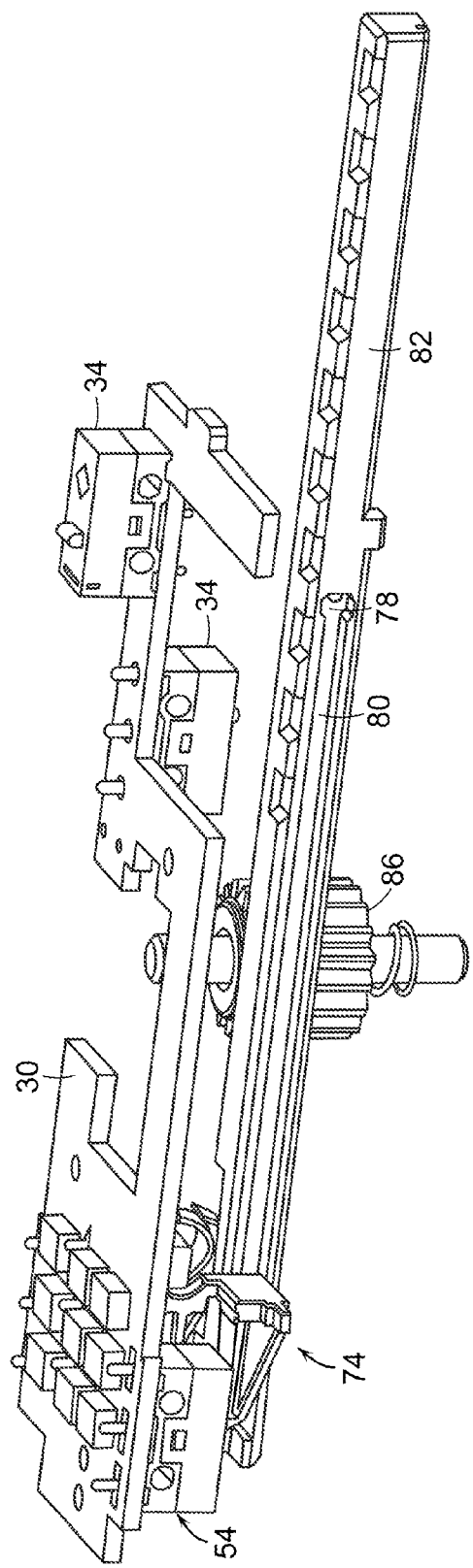
FIG. 4 is a downward-looking, front side perspective view of a direction control assembly of the surgical instruments according to various embodiments, showing, among other things, the direction control switch, the slider, the rack, and the pinion.
Figure 5:
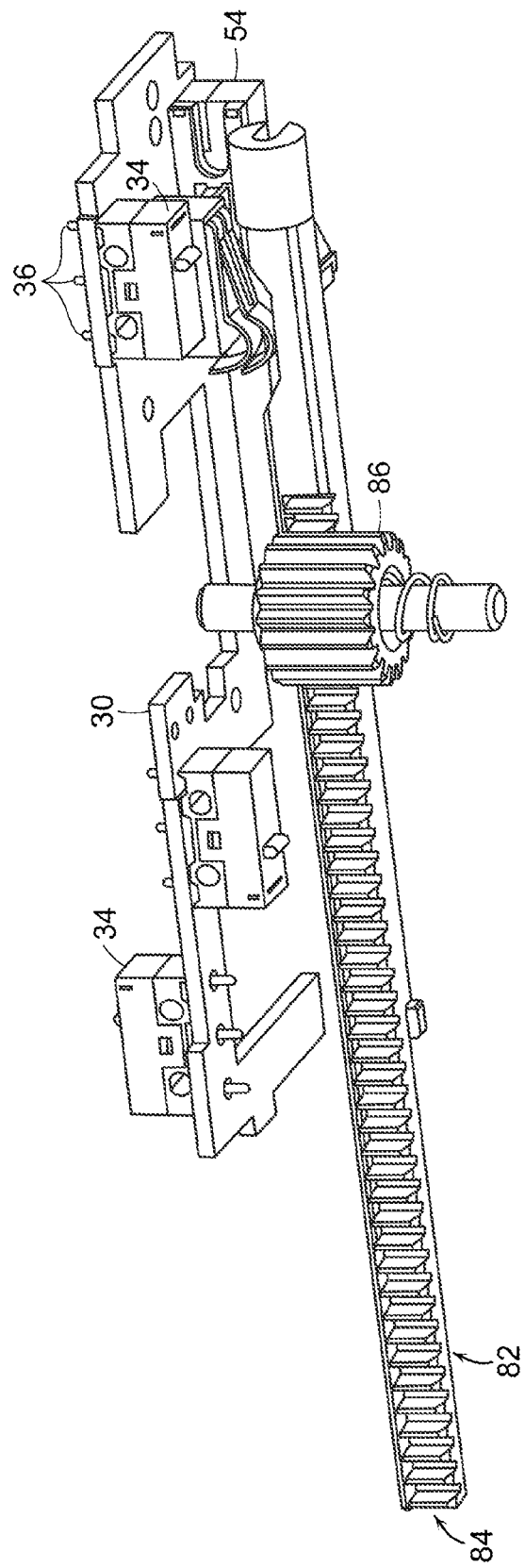
FIG. 5 is an upward-looking, back side perspective view of the direction control assembly of FIG. 4 according to various embodiments.
Figure 6:
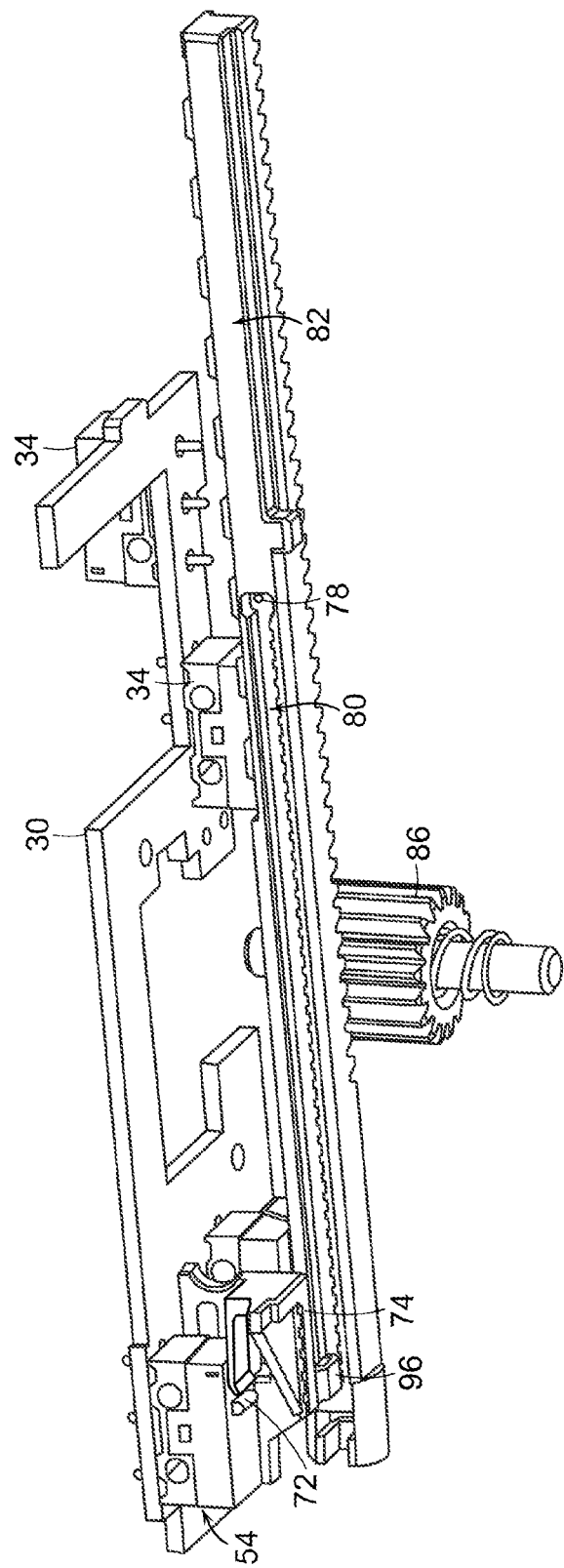
FIG. 6 is an upward-looking, front side perspective view of the direction control assembly of FIG. 4 according to various embodiments.
Figure 7:
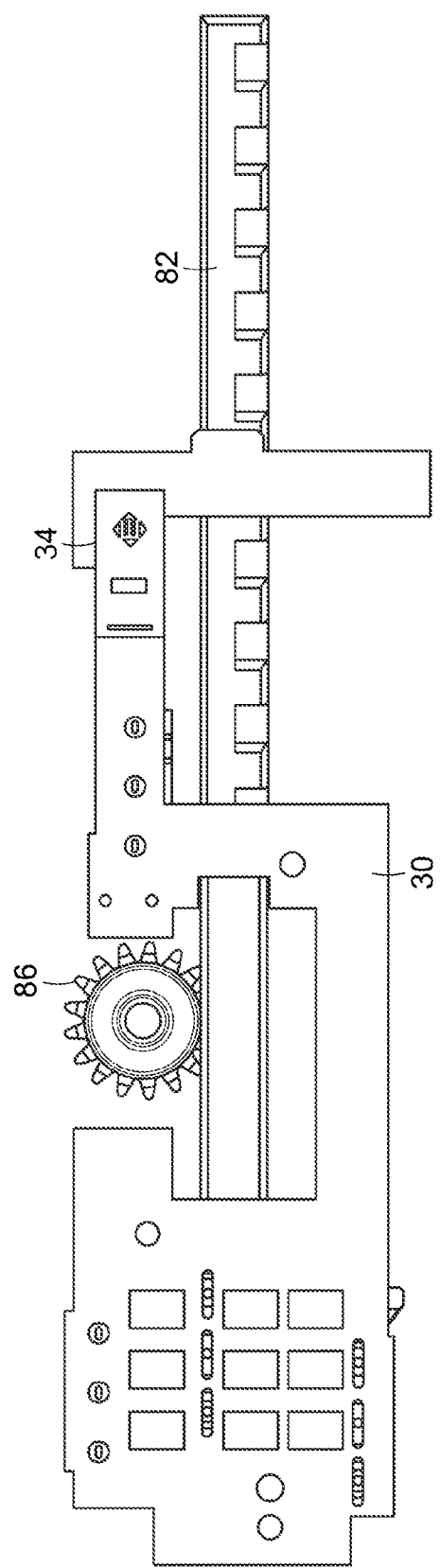
FIG. 7 is top side view of the direction control assembly of FIG. 4 according to various embodiments.
Figure 8:
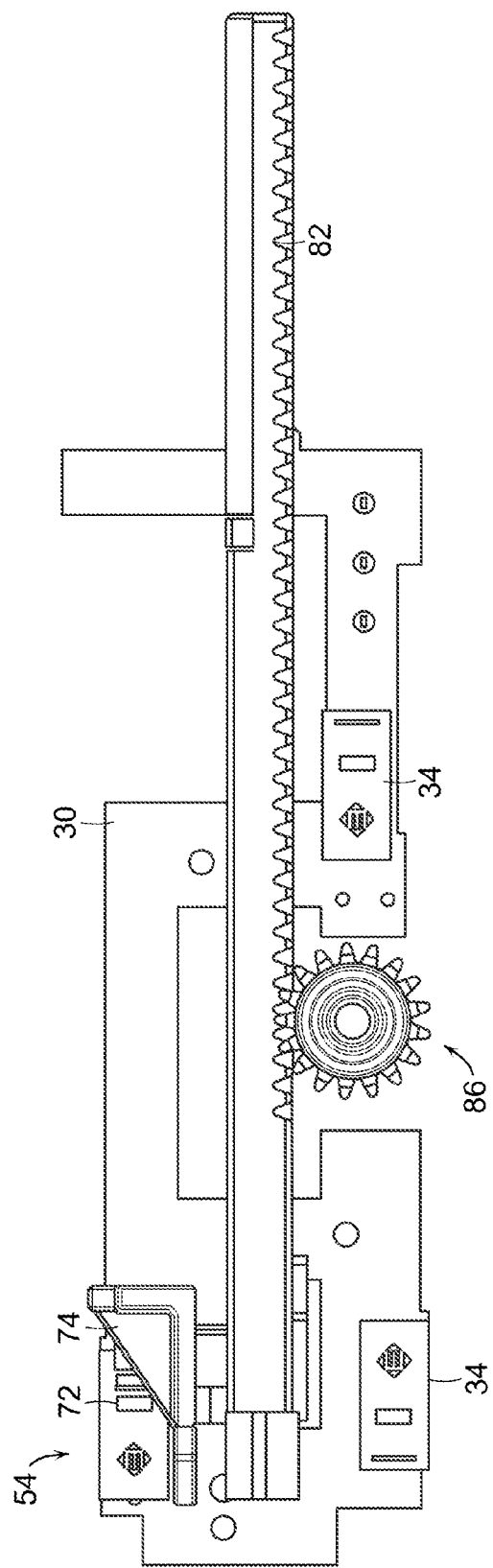
FIG. 8 is a bottom side view of the direction control assembly of FIG. 4 according to various embodiments.
Figure 9:
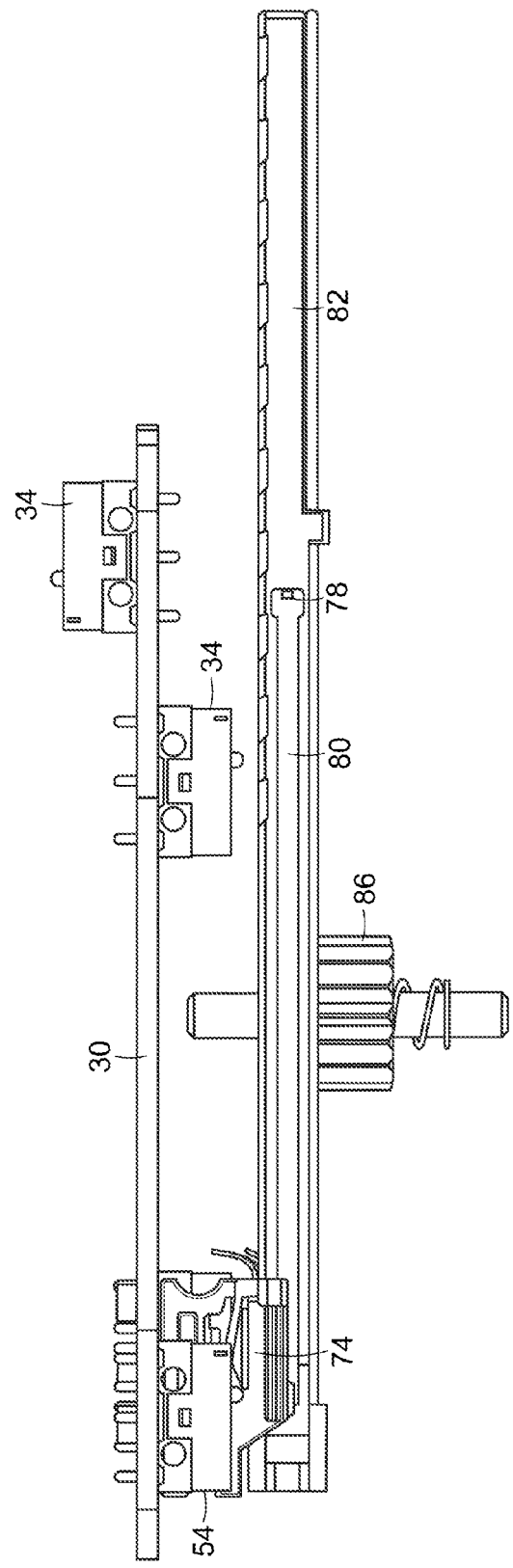
FIG. 9 is a front side view of the direction control assembly of FIG. 4 according to various embodiments.
Figure 10:
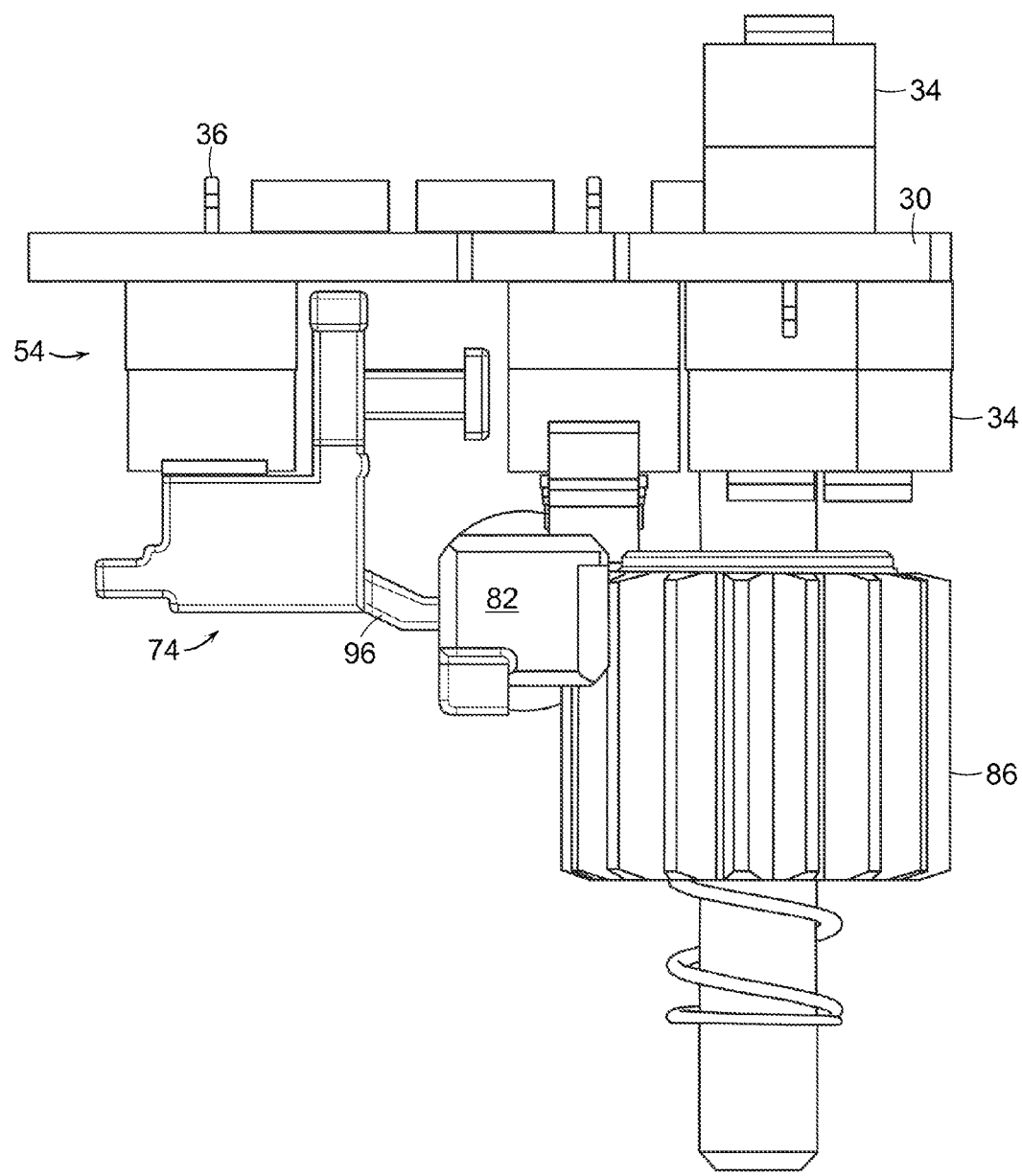
FIG. 10 is a proximate side view of the direction control assembly of FIG. 4 according to various embodiments.
Figure 11:
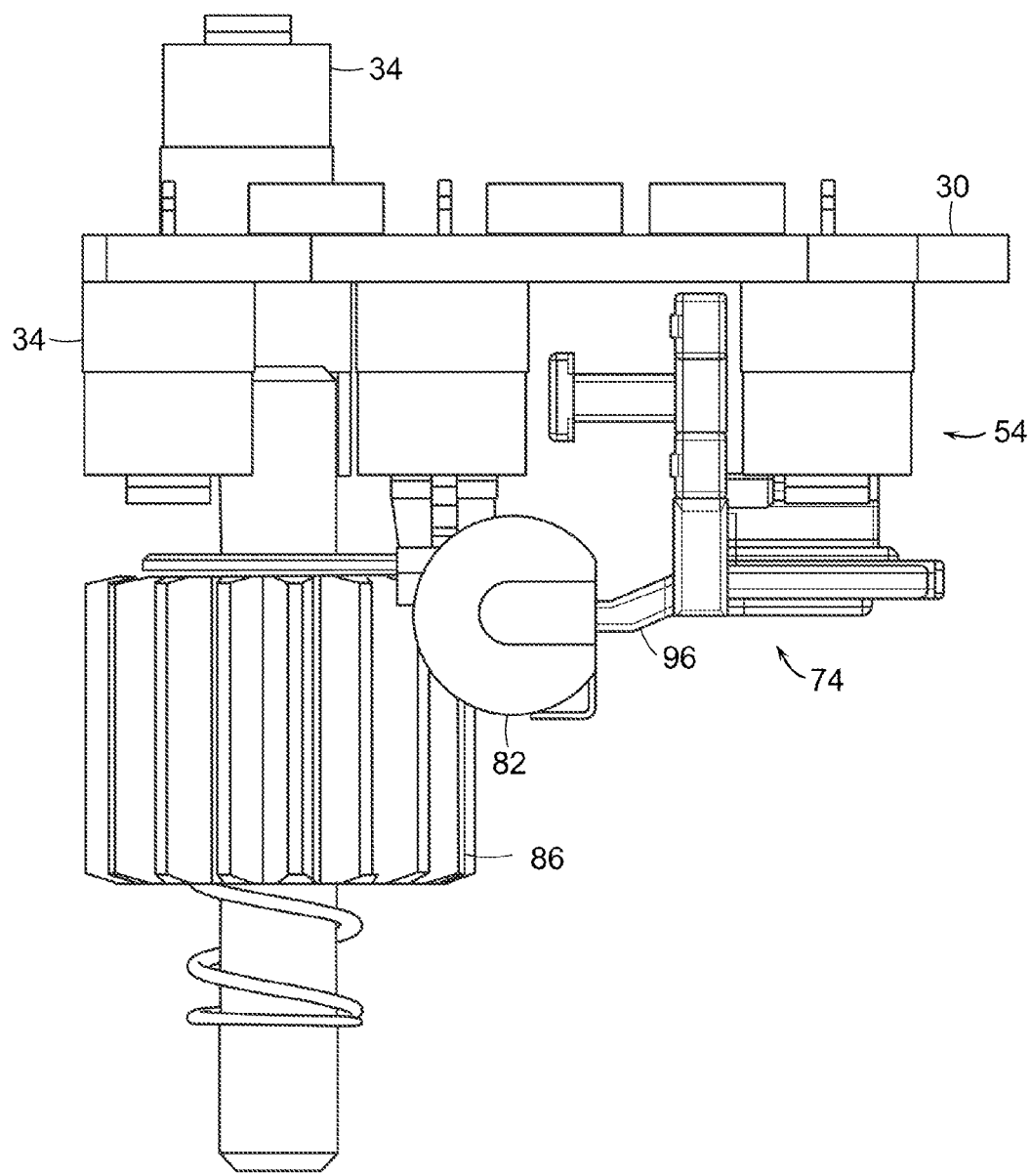
FIG. 11 is a distal side view of the direction control assembly of FIG. 4 according to various embodiments.
Figure 12:
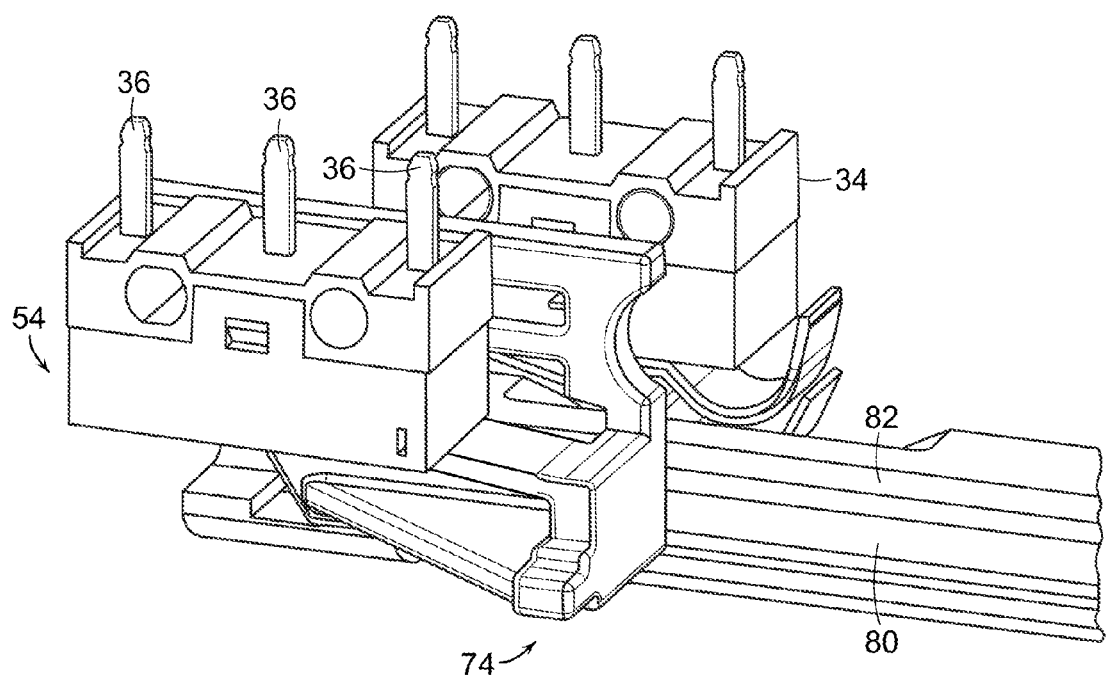
FIG. 12 is a downward-looking, front side, perspective view of the direction control switch, the slider, and the rack of the direction control assembly according to various embodiments.
Figure 13:
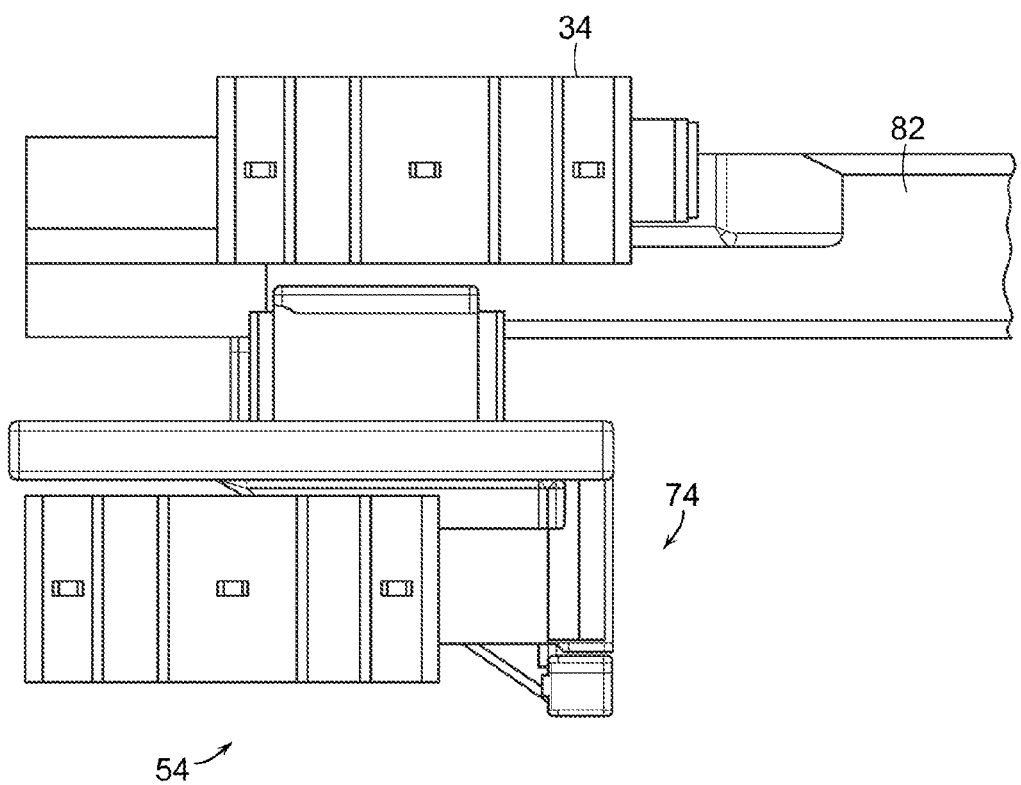
FIG. 13 is top view of the direction control switch, the slider, and the rack of the direction control assembly according to various embodiments.
Figure 14:
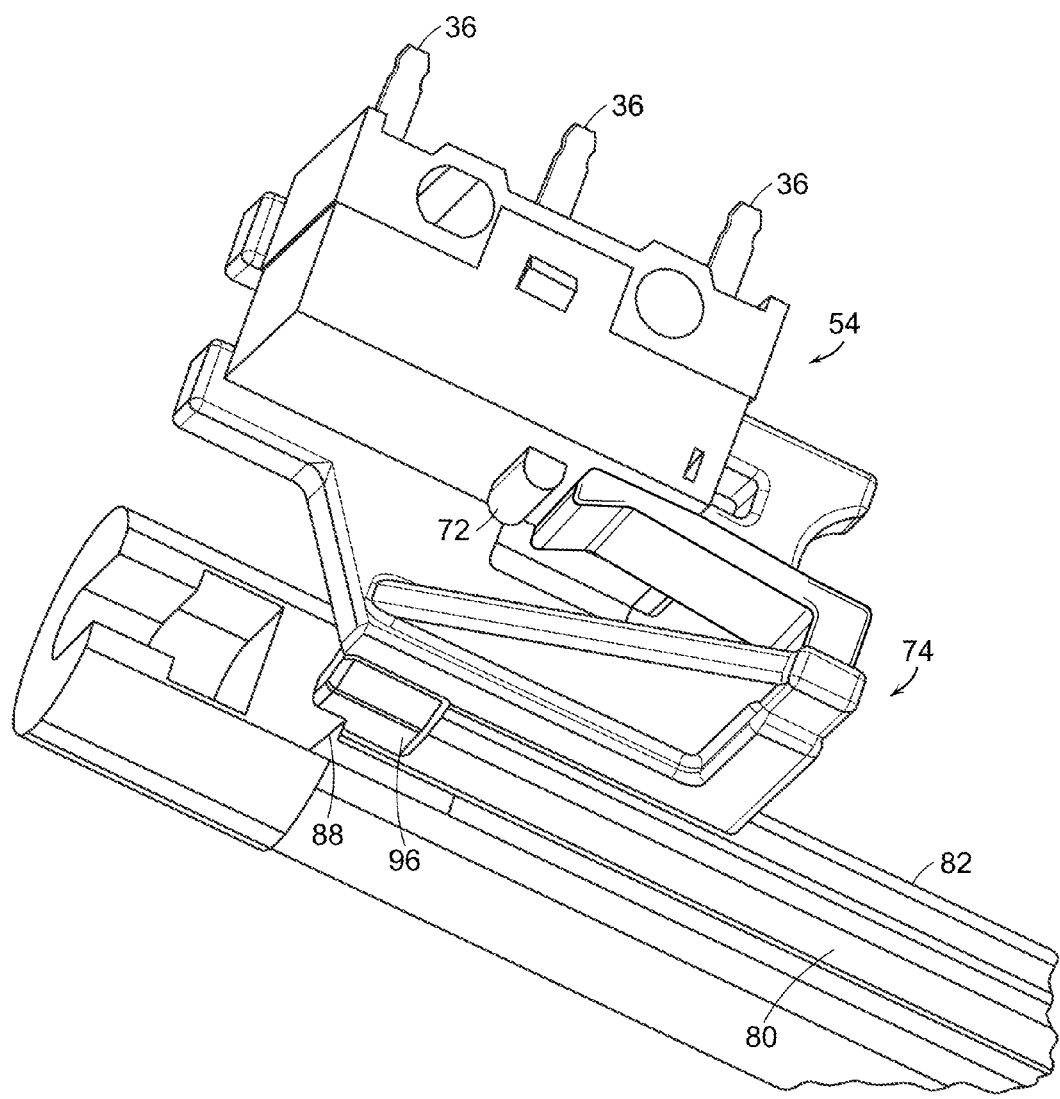
FIG. 14 is an upward-looking, front side, perspective view of the direction control switch, the slider, and the rack of the direction control assembly according to various embodiments.
Figure 15:
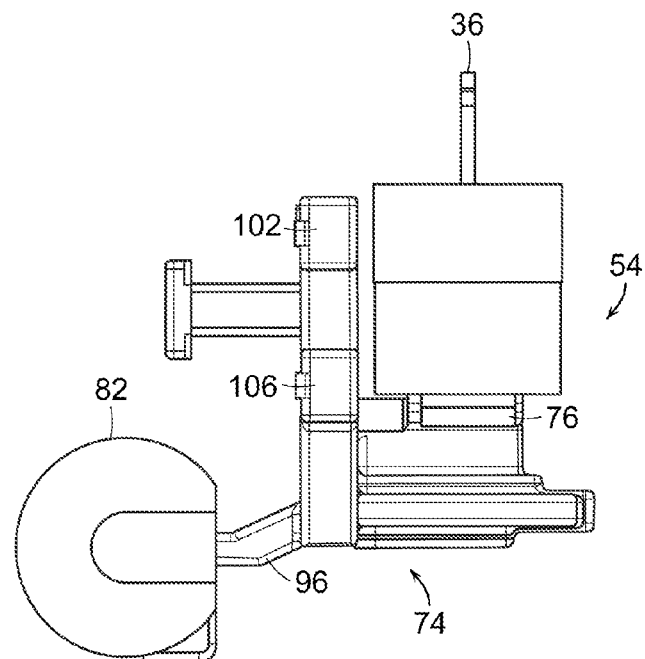
FIG. 15 is a distal side view of the direction control switch, the slider, and the rack of the direction control assembly according to various embodiments.

FIG. 3 is a schematic diagram of a control circuit 40 used to power the electric motor 42 with electrical power from a battery pack 44. In the illustrated embodiment, when a run motor (or fire) switch 46 is closed (it is shown in an open state in FIG. 3), and when a safety switch 48 is closed (it is shown open in FIG. 3), indicating that the device safety is set, and when a normally-closed lockout switch 50 is open, indicating that the instrument 10 is not in a lock-out condition, current flows through the safety switch 48, through a lockout indicator 52 (which may be a LED as shown in FIG. 3, that is located on the outside of the handle 6 such that it is visible to the operator of the instrument 10) to the motor 42. The run motor (or fire) switch 46 may be activated (or closed) when the operator of the instrument 10 retracts the firing trigger 20.

When the end of the cutting stroke is reached, that is, for example, when the cutting instrument in the end effector reaches the end of its cutting stroke, an end-of-stroke or direction switch 54 is switched to a closed position, reversing the polarity of the voltage applied to the motor 42 to thereby reverse the direction of rotation of the motor 42 (with the fire switch 46 also having been released or opened by the operator). In this state, current also flows through a reverse direction indicator 56, such as an LED that is located on the exterior of the handle 6 to provide a visual indication to the operator that the motor 42 direction has been reversed.

As shown in FIG. 3, the circuit may also comprise a manual return switch 58. The operator may manually flip this switch 58 if the cutting instrument in the end effector 12 has only been partially fired. Switching the manual return switch 58 may cause the motor 42 to reverse rotate, causing the cutting instrument to return to its original or home position. The switches of the motor control circuit 40 are not embodied as a part of a semiconductor-based integrated circuit (IC) according to various embodiments. For instance, in various embodiments, each of the switches may be separate microswitches or other suitable non-IC switches.

Additional embodiments for the motor control circuit 40 may be found in U.S. Pub. No. 2010/0076474, which is incorporated herein by reference in its entirety.

FIGS. 4-15 are views of a directional control assembly 70 for actuating a switch, such as the direction switch 54, of the motor control circuit 40 according to various embodiments of the present invention. The direction switch 54 may comprise, for example, a board-mountable microswitch that may be mounted on a lower surface of a circuit board 30 by pins 36. The circuit board 30 may be located in the upper portion 28 of the handle 6 (see FIGS. 1-2). Other circuit components for the motor control circuit 40 may be mounted to the circuit board 30 with conductive traces on the circuit board 30 connecting the components. For example, other switches of the motor control circuit 40 may also comprise board-mountable microswitches that are mounted to the circuit board 30, including either the upper and lower surfaces of the circuit board 30. The other electronic switches are shown in FIGS. 4-15 as element 34.

As shown more clearly in FIGS. 5-6 and 8-9, the direction switch 54 may comprise a moveable (e.g., depressible) switch actuator (e.g., plunger) 72. In various embodiments, when the depressible switch actuator 72 is depressed, the switch 54 is closed, thereby reversing the motor (with the fire switch 46 also having been released or opened by the operator). Conversely, when the depressible actuator 72 is undepressed, as shown in FIGS. 5-6 and 8-9, the direction switch 54 is open. Embodiments of the present invention are generally described herein where the directional control assembly 70 is used for actuating the direction switch of a motor control circuit, in a motor-driven surgical instrument, although it should be noted that the control assembly 70 could be used to actuate a switch with another purpose in another type of device or instrument, and that the present invention is not limited to embodiments where the control assembly is used to actuate a motor direction switch.

Figure 16:
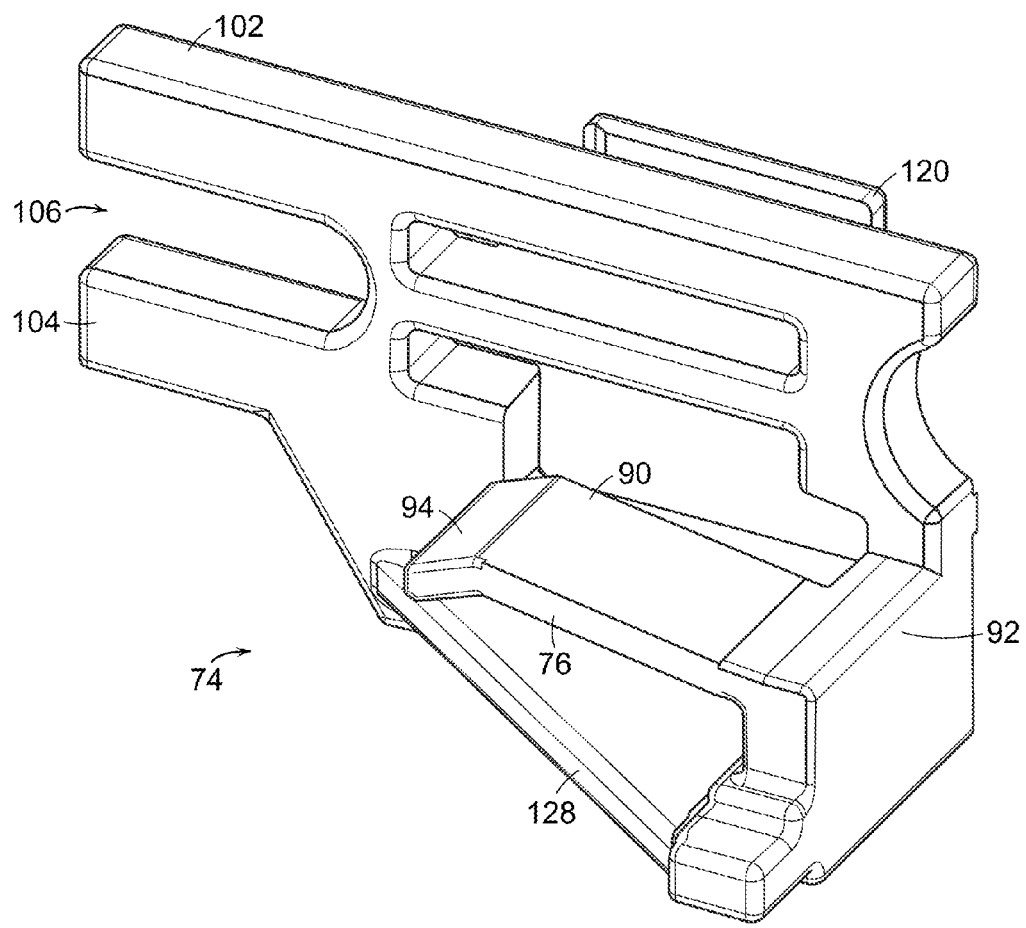
FIG. 16 is a downward-looking, front side, perspective view of the slider of the direction control assembly according to various embodiments.
Figure 17:
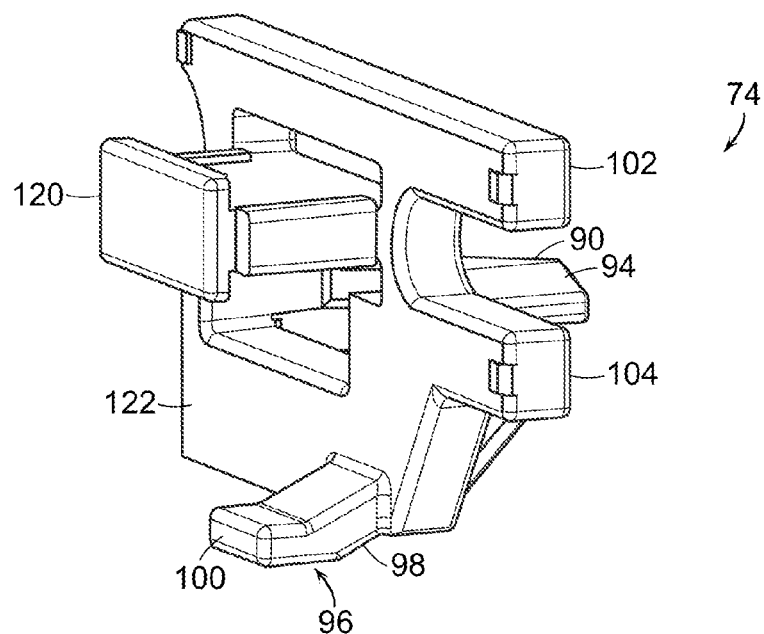
FIG. 17 is a back side, perspective view of the slider of the direction control assembly according to various embodiments.
Figure 18:
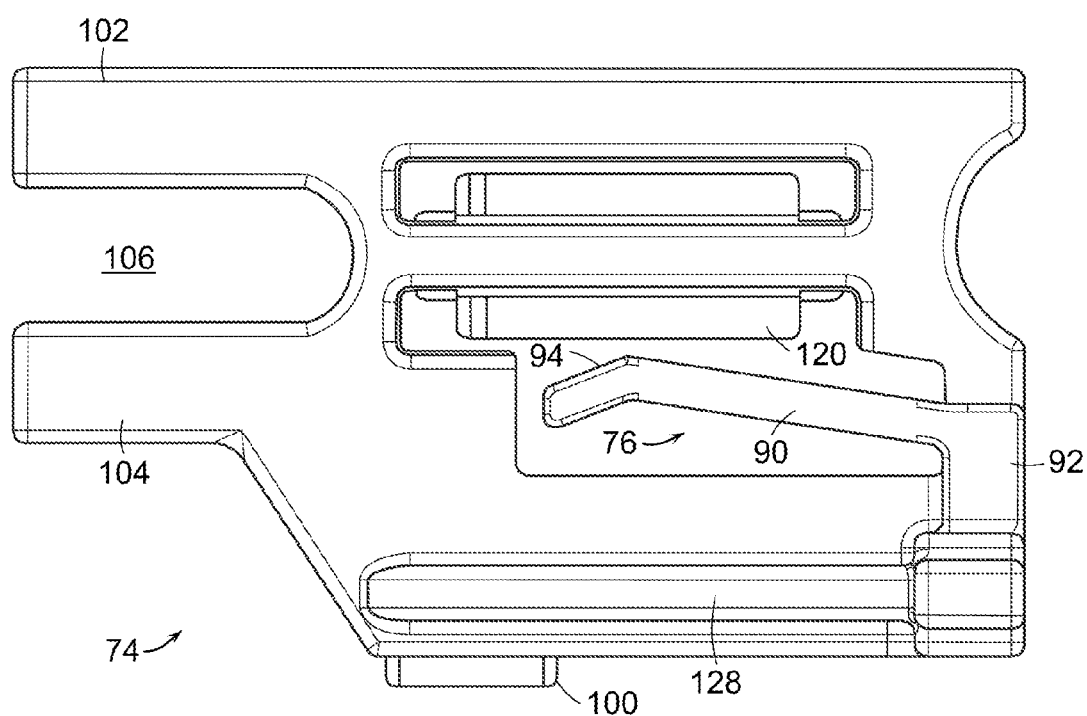
FIG. 18 is a front side view of the slider of the direction control assembly according to various embodiments.
Figure 19:
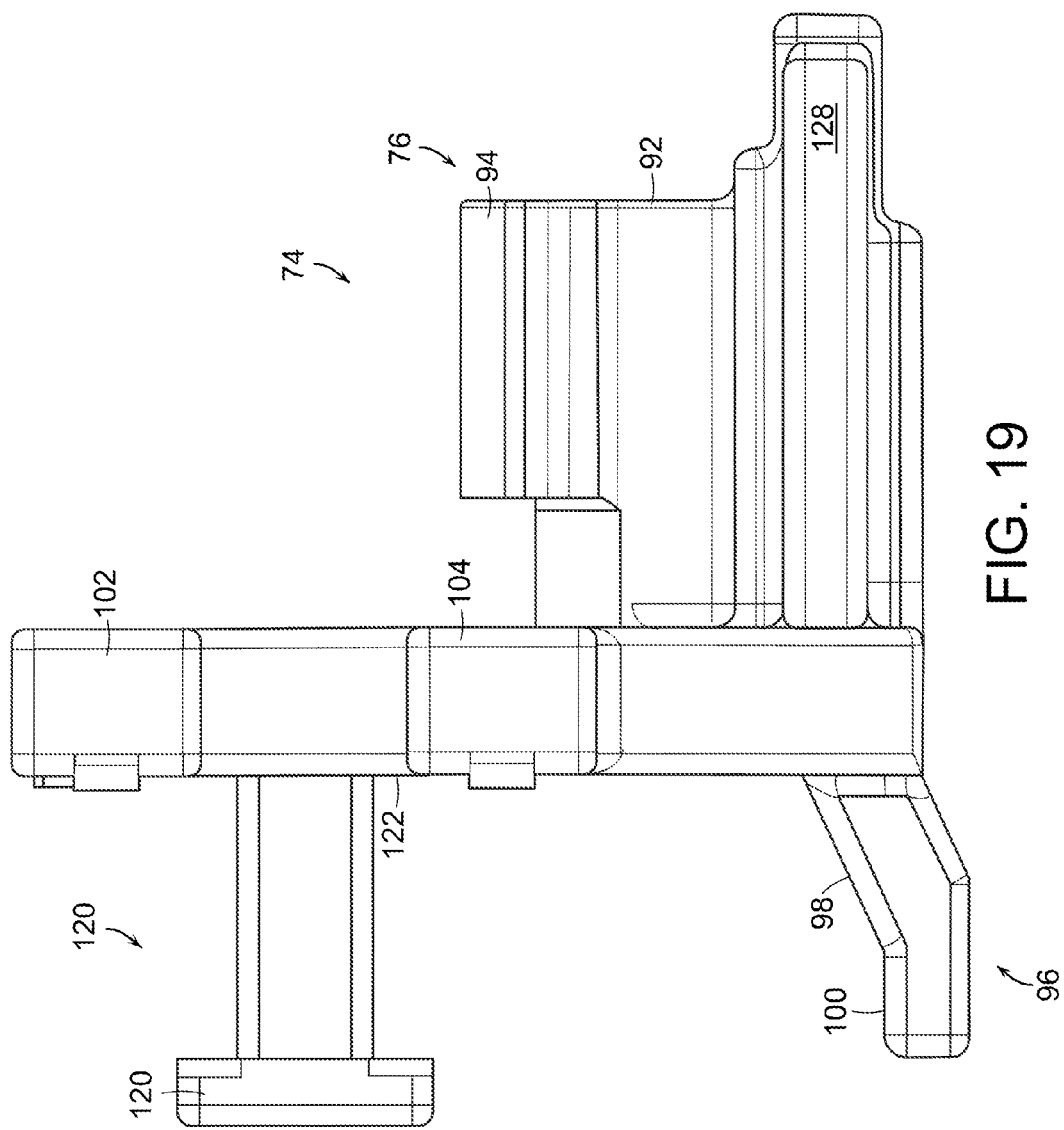
FIG. 19 is a distal side view of the slider of the direction control assembly according to various embodiments.

The depressible switch actuator 72 may be depressed, or actuated, by a slider 74, which may be made from a single piece of injection molded plastic, for example. In other embodiments, the slider 74 may comprise a combination of multiple, separate parts; some of parts may be made from materials other than plastic. FIGS. 16-19 provide view of the slider 74 according to various embodiments. FIG. 16 is a front perspective view; FIG. 17 is a back perspective view; FIG. 18 is a front view; and FIG. 19 is a distal side view. As shown in the illustrated embodiment, the slider 74 may comprise a cantilevered arm 76. As shown in FIGS. 4-15, the cantilevered arm 76 of the slider 74 engages the depressible switch actuator 72 of the switch 54 when the slider 74 is urged, or pushed, distally by a proximate-side channel shoulder 78 at a proximate side of a channel 80 defined by the front side of a rack 82. The back side of the rack 82 may comprise a series of teeth 84 that mesh with grooves of a pinion 86. The pinion 86 is geared to, and rotated by, an output gear of the motor 42. In that way, the rack 82 may be translated longitudinally, either distally or proximately, by rotation, either forward or reverse, of the pinion 86.

As seen in FIGS. 5-6, 9, 11, 13-15, the distal end of the rack 82 may define an opening 38 for receiving the proximate end of the drive shaft that drives the end effector 12. FIGS. 36-37 show the proximate end 148 of the drive shaft 150 positioned in the opening 38 of the rack 82. In such a configuration, longitudinal movement of the rack 82 (caused by rotation of the pinion 86, which is caused by rotation of the motor 42) causes the drive shaft 150 to move longitudinally, to thereby actuate (or deactuate) components of the end effector 12, such as the cutting instrument 154.

When the rack 82 is moved proximately, a distal-side channel shoulder 88 of the channel 80 may urge of push the slider 74 proximally, to thereby move the slider such that its cantilevered arm 76 is out of engagement with the actuator 72, so that the actuator 72 is not depressed, so that the direction switch 54 is in the open position.

As shown, for example, in FIGS. 16-19, the cantilevered arm 76 may comprise a first, upwardly sloping portion 90 extending from a base portion 92 of the slider 74, and a second, downwardly sloping portion 94 extending from the first portion 90. When the slider 74 is urged or pushed distally, the second portion 94 of the cantilevered arm 76 may engage and depress the depressible actuator 72 on the switch 54. In various embodiments, the slider 74 may be pushed distally such that the second portion 94 is pushed distally past the actuator 72 so that the actuator 72 is held in the depressed position by the first portion 90 of the cantilevered arm 76.

Also as shown in FIGS. 16-19, the slider 74 may comprise an integrated tab 96 that extends rigidly from the slider 74. The tab 96 may comprise a first portion 98 that extends from a back portion 122 of the slider 74 and a second portion 100 that extends from the first portion 98. The second portion 100 of the tab 96 may sit movably in the channel 80 of the rack 82, as shown in FIGS. 6, 10-11, and 14-15. The tab 96 may be pushed by either the proximate-side channel shoulder 78 or the distal-side channel shoulder 88 of the channel 80 when the rack 82 is moved longitudinally distally or proximately, respectively, to thereby move the slider 74 distally or proximately with the tab 96.

The slider 74 may also comprise a brace portion 128 extending between the base portion 92 and the back portion 122. The brace portion 128 may provide structural stability to the slider 74, reducing relative movement between the back portion 122 and the base portion 92. As shown in the figures, in various embodiments the brace portion 128 may be orthogonal to both the back portion 122 and the base portion 92.

FIGS. 4, 6, 9, 12, and 14 show the slider 74 at the distal end of the channel 80 of the rack 82. In this position, when the rack 82 is moving proximately, the distal-side channel shoulder 88 engages the tab 96 of the slider 74, pushing the tab 96, and thereby the slider 74, to its most proximate position, in which the depressible actuator 72 on the switch is unactuated (e.g., not depressed). FIGS. 20 and 21 show the slider 74 at the proximate end of the channel 80 of the rack 82. In this position, when the rack 82 is moving distally, the proximate-side channel shoulder 78 engages the 76 of the slider 74, pushing the tab 96, and thereby the slider 74, to its most distal position, in which the depressible actuator 72 on the switch 54 is actuated (e.g., depressed).

In such a manner, after the slider 74 is moved distally to actuate the switch 54, the slider 74 stays at its distal-most position and the switch 54 remains actuated by the slider 74 even when the rack 82 changes direction and moves proximately, until the distal-side shoulder 88 engages the tab 96 and moves the slider 74 proximately so that the slider 74 no longer actuates the switch 54. Similarly, after the slider 74 is moved proximately so that it no longer actuates the switch 54, the slider 74 remains disengaged from the switch 54 such that the switch 54 remains unactuated, even when the rack 82 changes direction and moves proximately, until the proximate-side shoulder 78 engages the tab 96 and moves the slider 74 back to is distal-most, switch-actuating position.

Also as shown in FIGS. 16-19, the slider 74 may comprise an upper arm 102 and a lower arm 104 that define a U-channel 106. The U-channel 106 may engage a stopper on a frame that supports the circuit board 30 when the slider 74 is pushed to its most distal position, as described further below. The stopper may tightly fit in the U-channel 106 such that the tightness of the fit keeps the slider 74 in the distal-most position even when the rack 82 is moving proximately. In various embodiments, the force from the distal channel shoulder 88 against the tab 96 is sufficient to disengage the U-channel 106 from the stopper on the frame, thereby allowing the slider 74 to be pushed by the distal channel shoulder 88 from its distal position (shown in FIGS. 4, 6, 9, 12, and 14) to its proximate position (shown in FIGS. 20-21). In that way, the slider 74 does not move with the rack 82, but only when the either of the channel shoulders 78, 88 of the rack 82 engage the tab 96 disposed in the rack channel 80, thereby pushing the slider 74.

Figure 22:
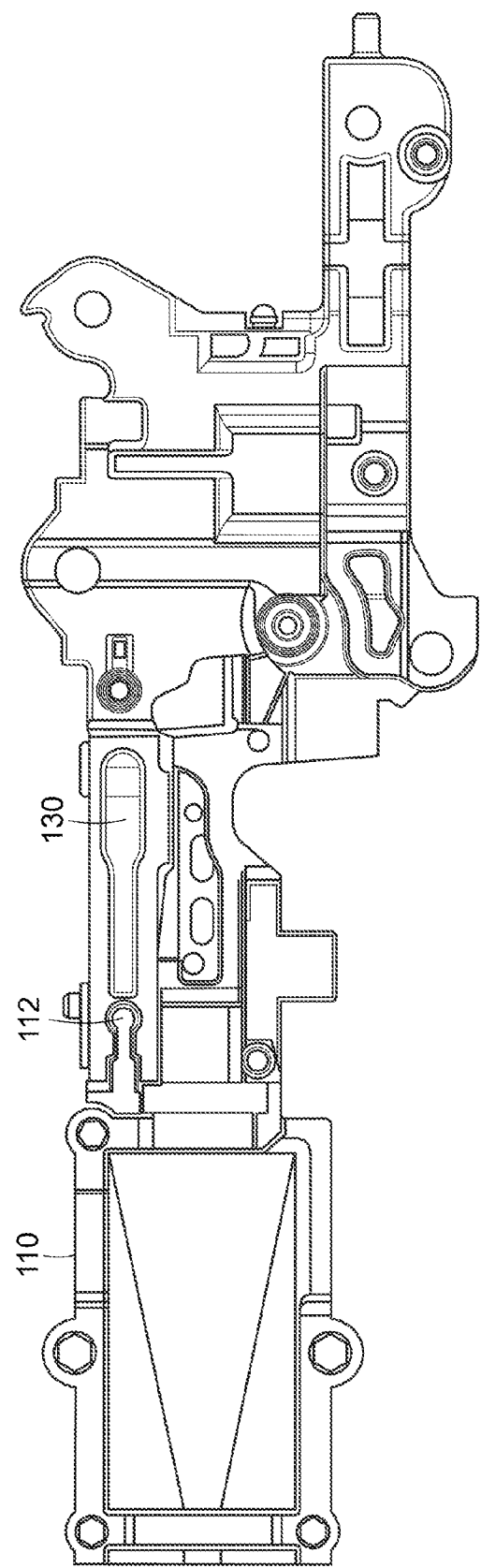
FIG. 22 is a front side view of the frame according to various embodiments.
Figure 23:
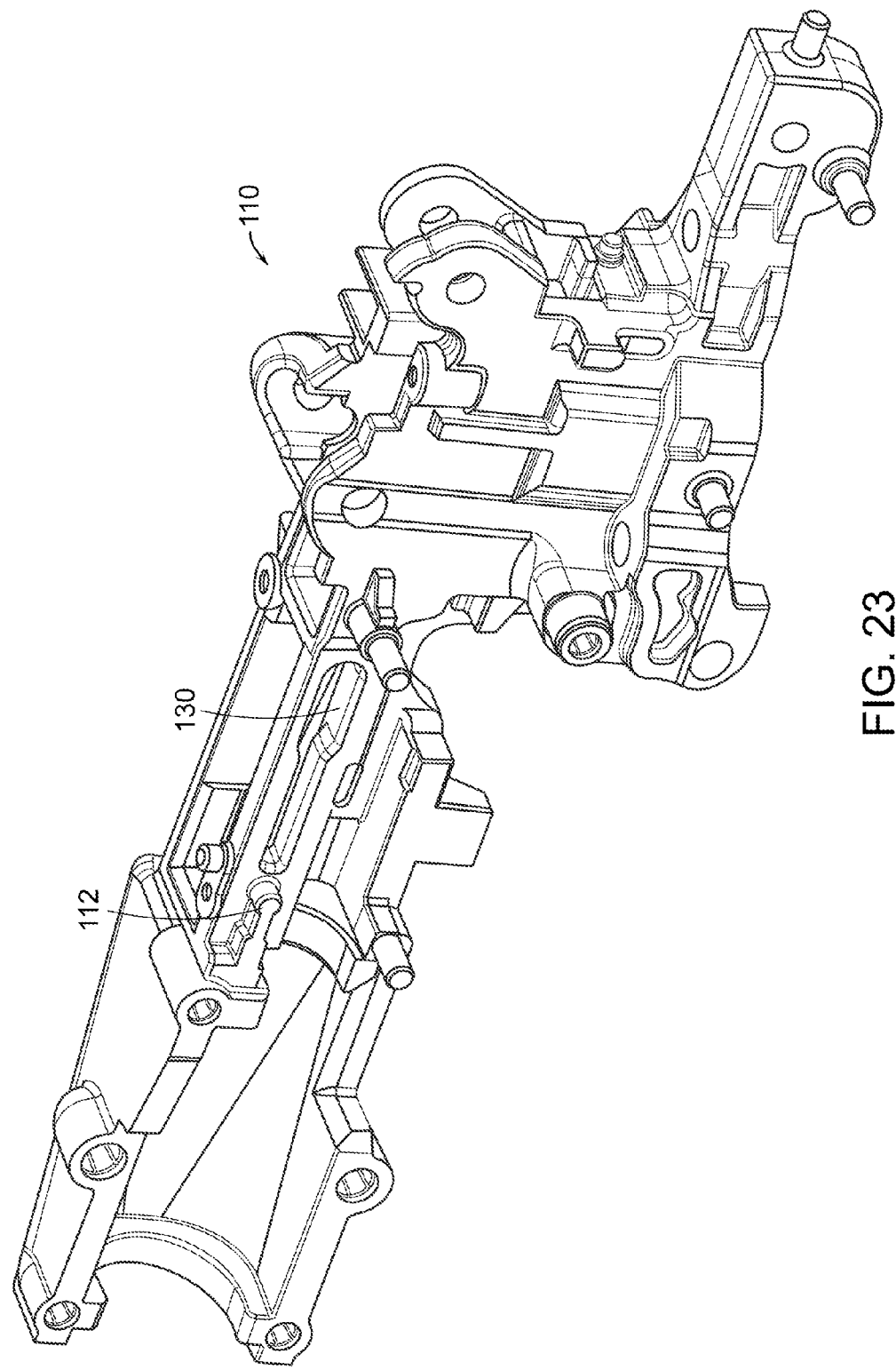
FIG. 23 is a front side, perspective view of the frame according to various embodiments.

As mentioned above, the U-channel 106 defined by the slider 74 engages a stopper on a frame inside in the handle 6 of the instrument 10. FIGS. 22 and 23 show a portion of the frame 110 with the stopper 112. As shown in these figures, the stopper 112 may extend from a side of the frame 110 facing the slider 74. The stopper 112 may be shaped to fit snugly into the U-channel 106 defined by the slider 106 when the slider 74 is in its distal-most position. FIG. 22 is a side view of the frame 110 and FIG. 23 is a perspective view of the frame 110. The frame 110 may be constructed from plastic, for example. The instrument 10 may comprise a second frame piece (not shown) that connects to the frame 110.

Figure 24:
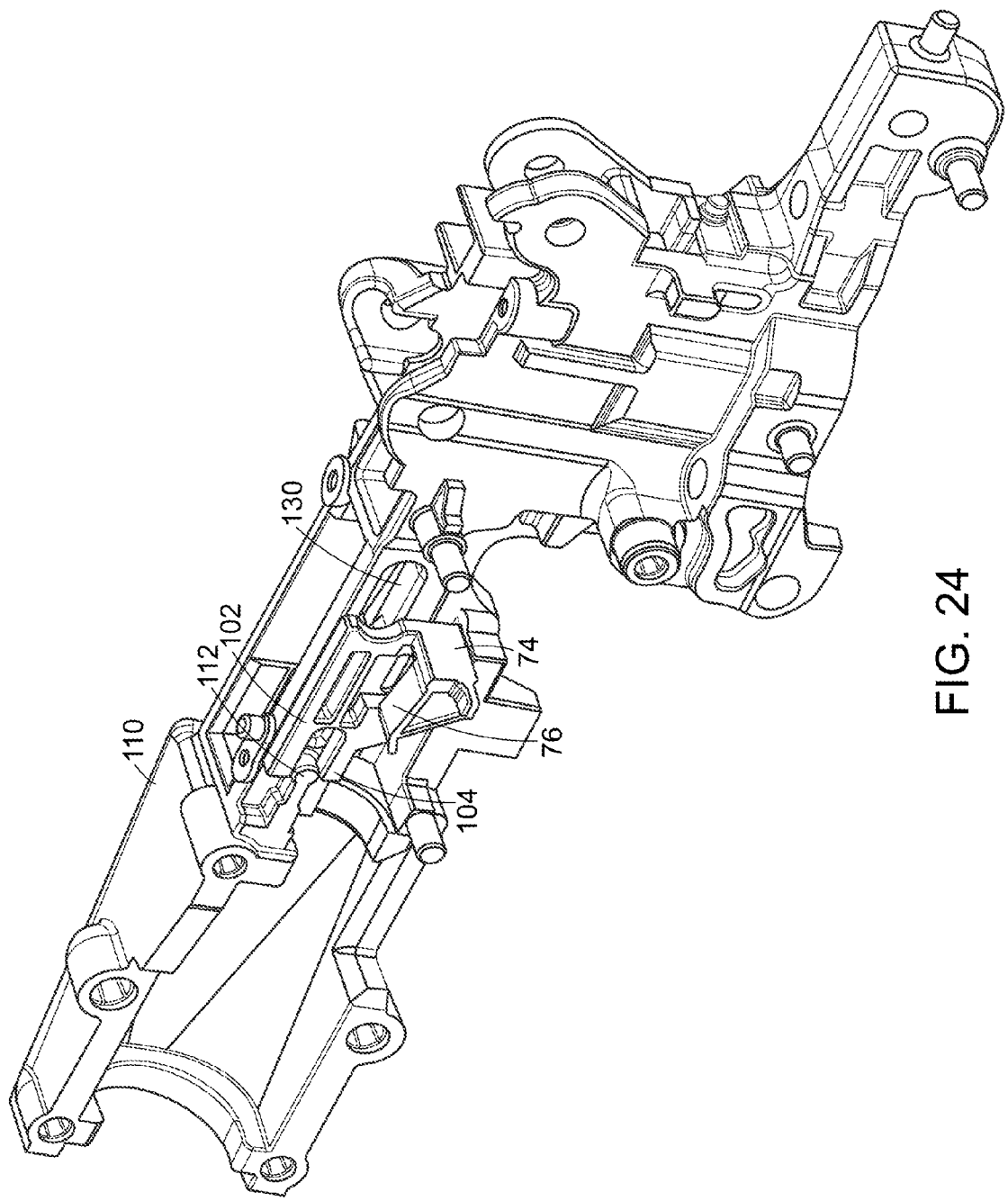
FIG. 24 is a front side, perspective view of the frame and the slider according to various embodiments.
Figure 25:
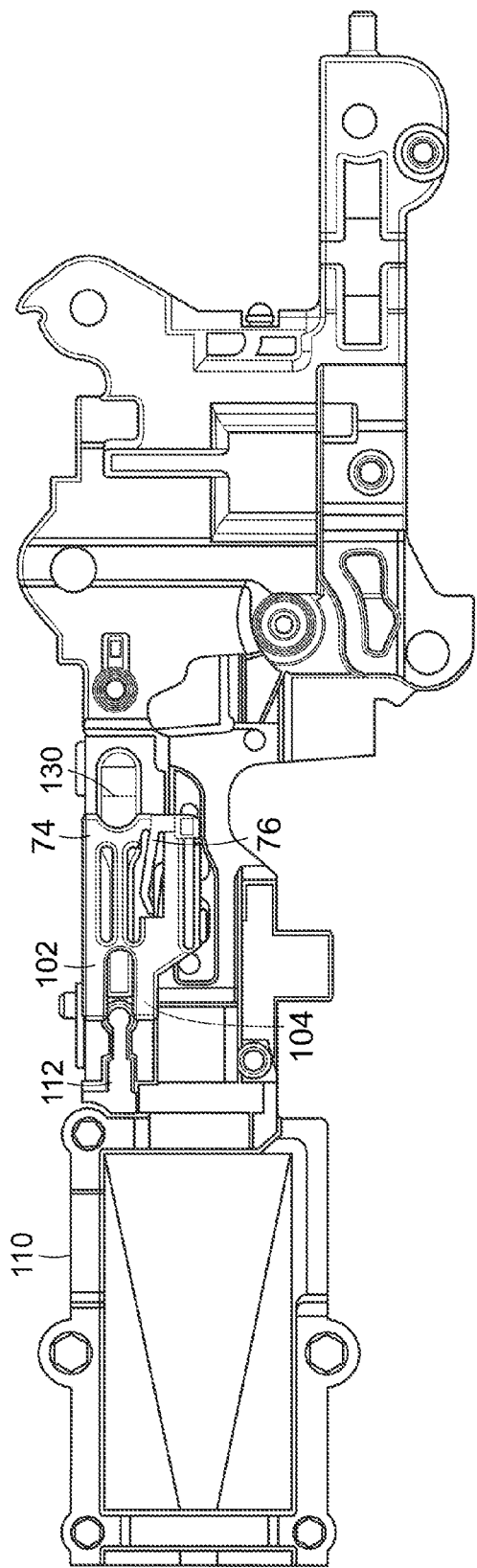
FIG. 25 is a front side view of the frame and the slider, with the slider in its proximate position, according to various embodiments.
Figure 26:
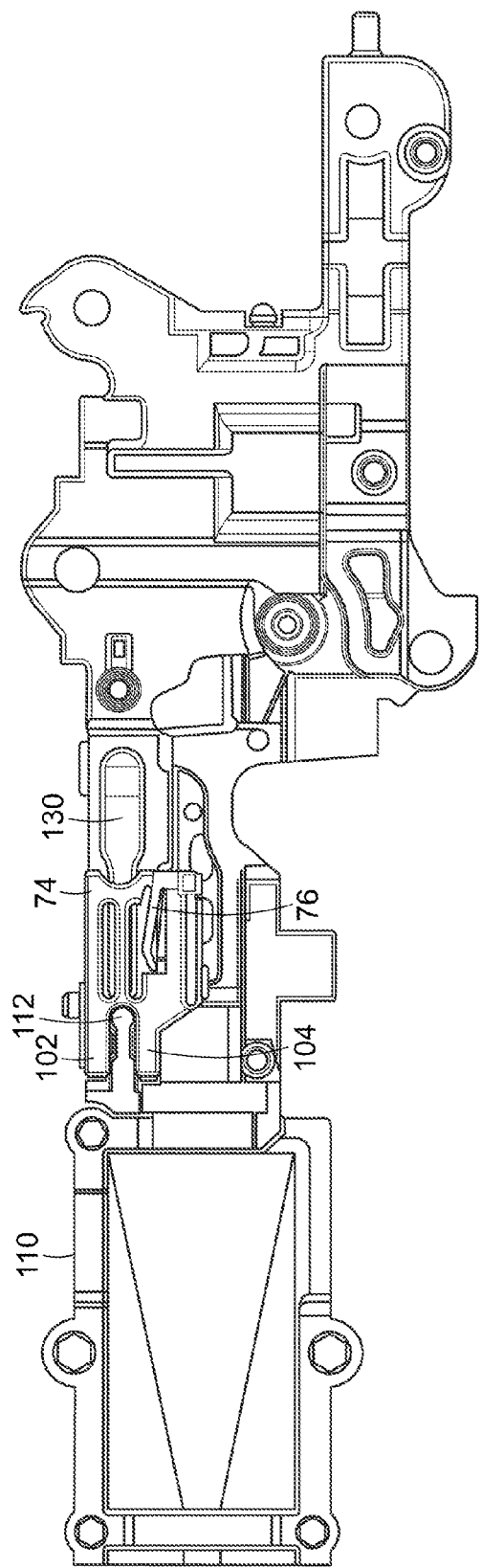
FIG. 26 is a front side view of the frame and the slider, with the slider in its distal position, according to various embodiments.

FIGS. 24-26 show both the frame 110 and the slider 74. Other components of the direction control assembly 70 are not shown in FIGS. 24-26 for convenience. FIG. 24 is a front perspective view of the frame 110 with the slider 74 in its proximate position such that the U-channel 106 is not engaged by the stopper 112 of the frame 110. FIG. 25 is a front side view with the slider 74 in the proximate position. When the slider 74 is in its proximate position, the cantilevered arm 76 of the slider 74 would not normally be depressing the depressible actuator 72 of the switch 54. Conversely, FIG. 26 is a front side view that shows the slider 74 in its distal-most position. When the slider 74 is in the distal-most position, the cantilevered arm 76 would normally be depressing the depressible actuator 72 of the switch 54.

As shown in FIGS. 16-19, the slider 74 may also comprise a frame tab 120 extending from the back portion 122 of the slider 74. The frame tab 120 may comprise a neck 124 and a head 126. The neck 124 may be disposed in a slot 130 in the side of the frame 110 facing the slider 74 (see FIGS. 22-27 for example). The slot 130 may confine the movement of the slider 74 relative the frame 110 as the rack 82 moves the slider 74 as described above.

Figure 27:
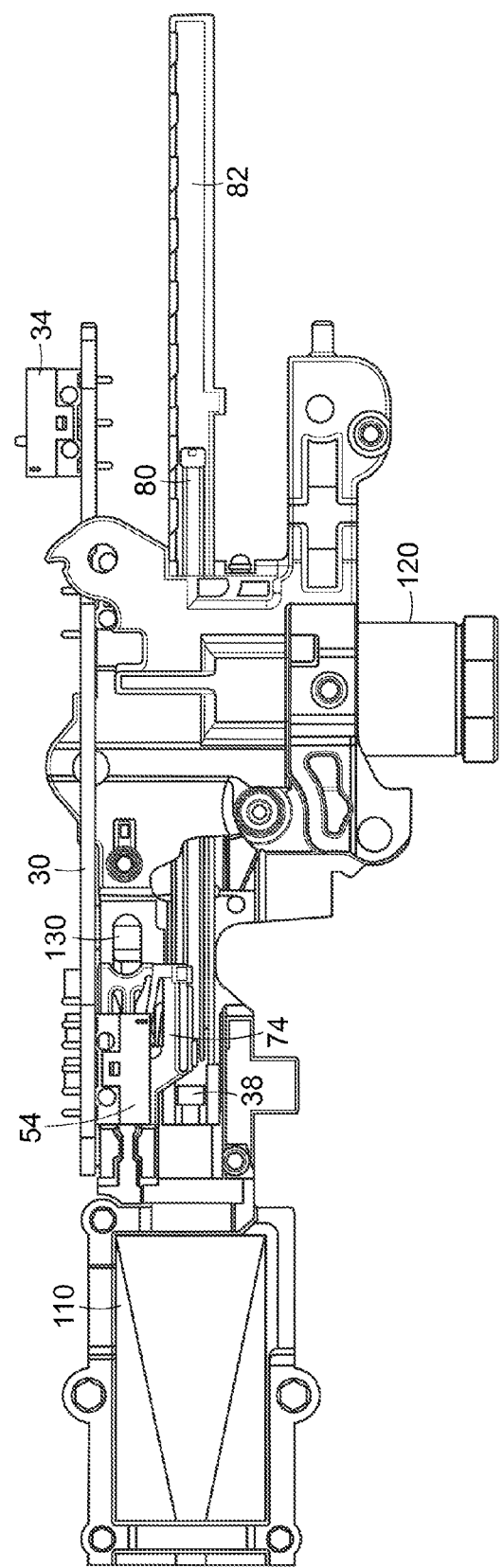
FIG. 27 is a front side view of the direction control assembly according to various embodiments, showing, among other things, the circuit board, the direction control switch, the slider, the rack, and the frame.
Figure 28:
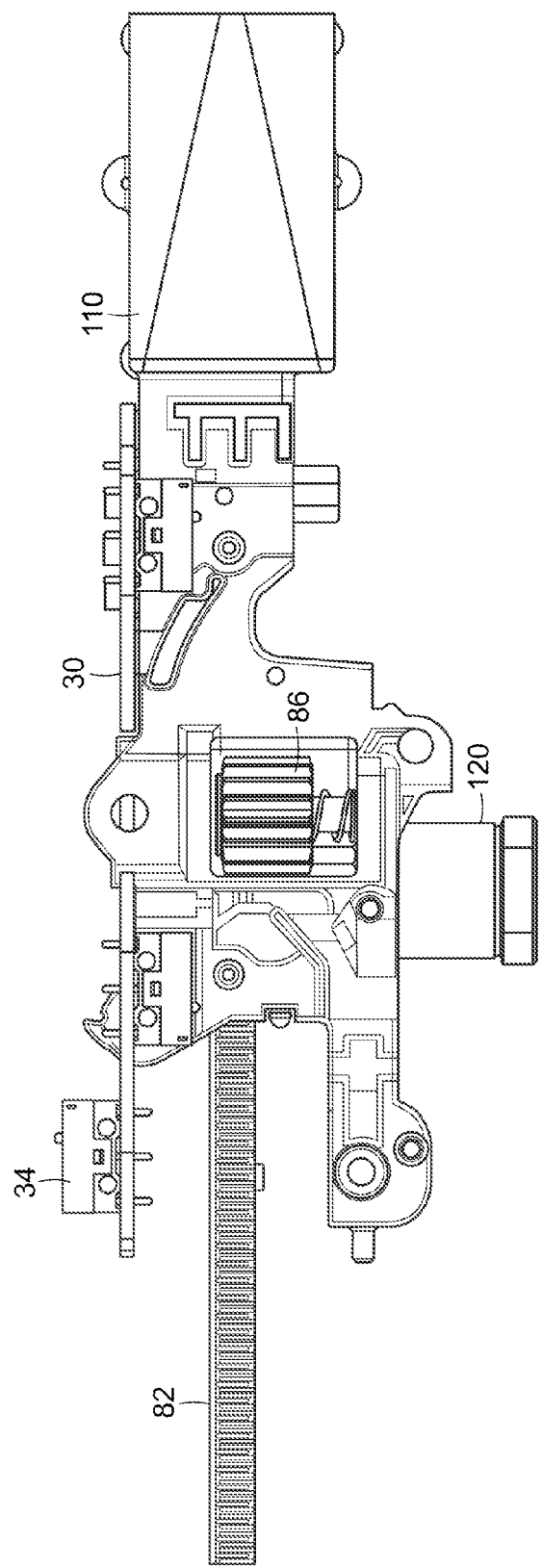
FIG. 28 is a back side view of the direction control assembly of FIG. 27 according to various embodiments.
Figure 29:
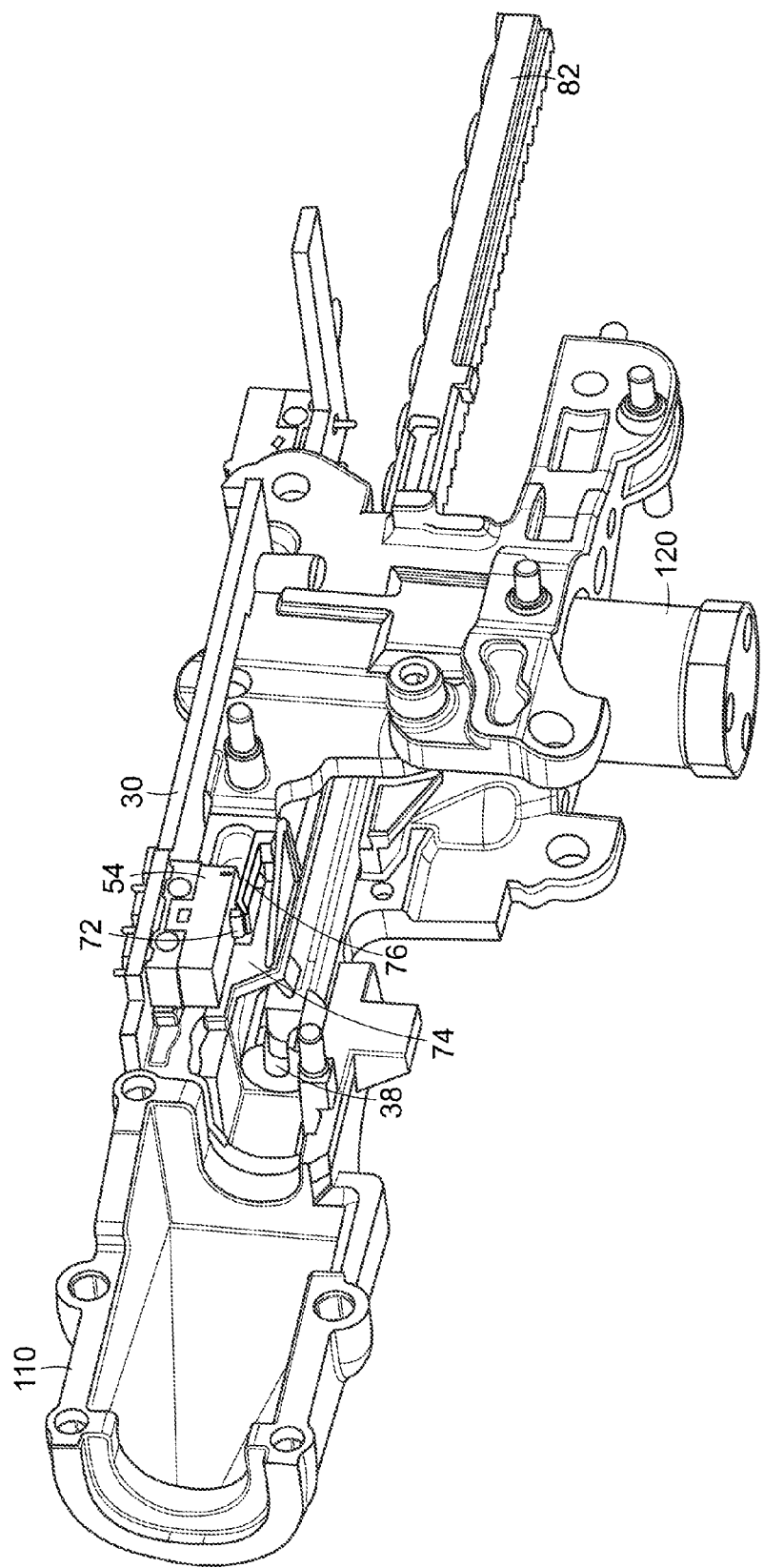
FIG. 29 is an upward-looking, front side, perspective view of the direction control assembly of FIG. 27 according to various embodiments.
Figure 30:
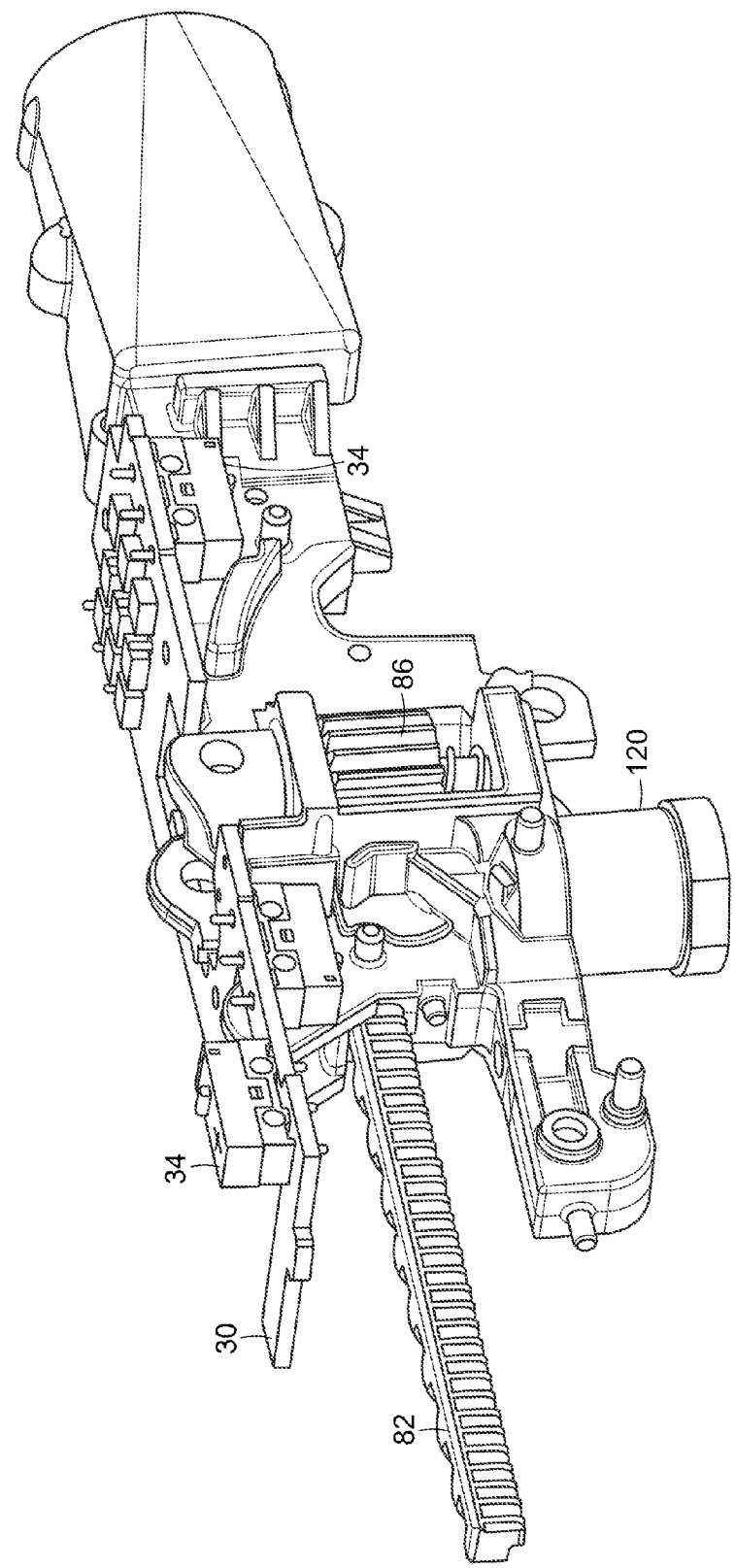
FIG. 30 is a back side perspective view of the direction control assembly of FIG. 27 according to various embodiments.
Figure 31:
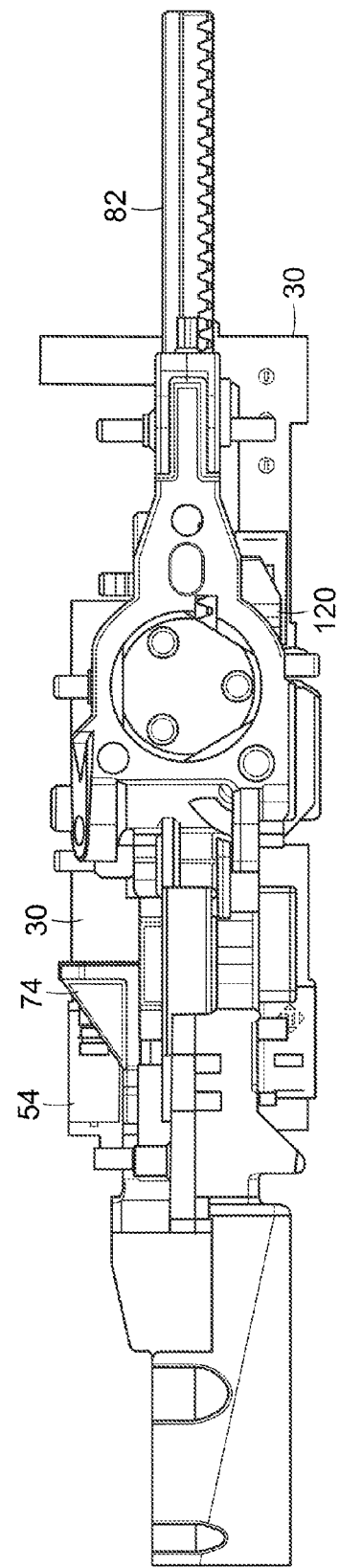
FIG. 31 is a bottom side view of the direction control assembly of FIG. 27 according to various embodiments.

FIGS. 27-31 show the frame 100 with the circuit board 30, the slider 74, the rack 82, and the pinion 86. The circuit board 30 may be connected to an upper surface of the frame 110, such as by screws or some other mounting technique. These figures also show portions of a gear assembly 120 that is geared to the pinion 86. The gear assembly 120 may couple the output drive shaft of the motor 42 to the pinion 86. FIG. 27 is a front side view; FIG. 28 is a back side view; FIG. 29 is a front side, distal perspective view; FIG. 30 is a back side, proximate perspective view; and FIG. 31 is a bottom side view.

Figure 32:
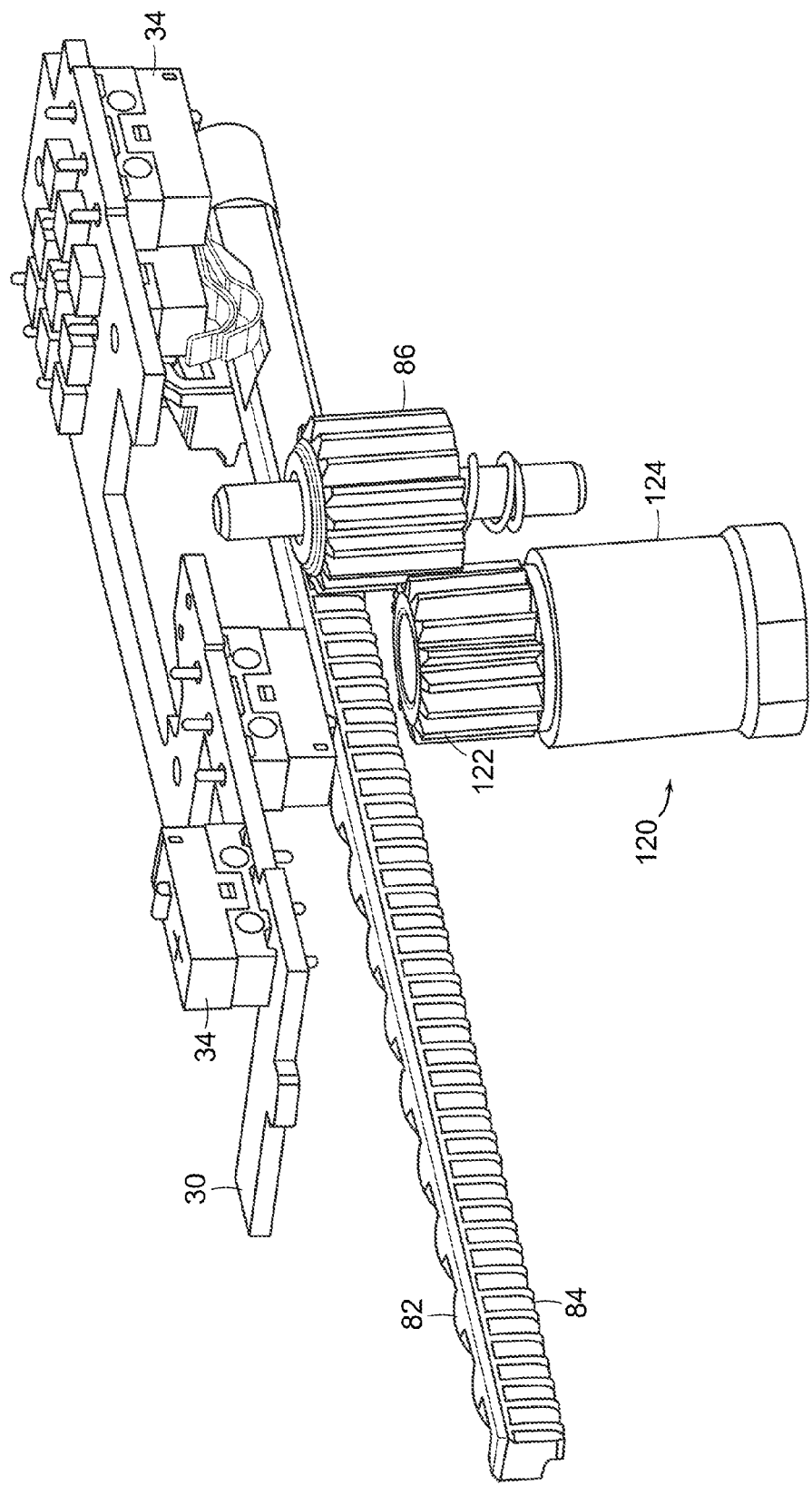
FIG. 32 is a back side, perspective view showing the circuit board, rack, pinion, and gear assembly according to various embodiments.
Figure 33:
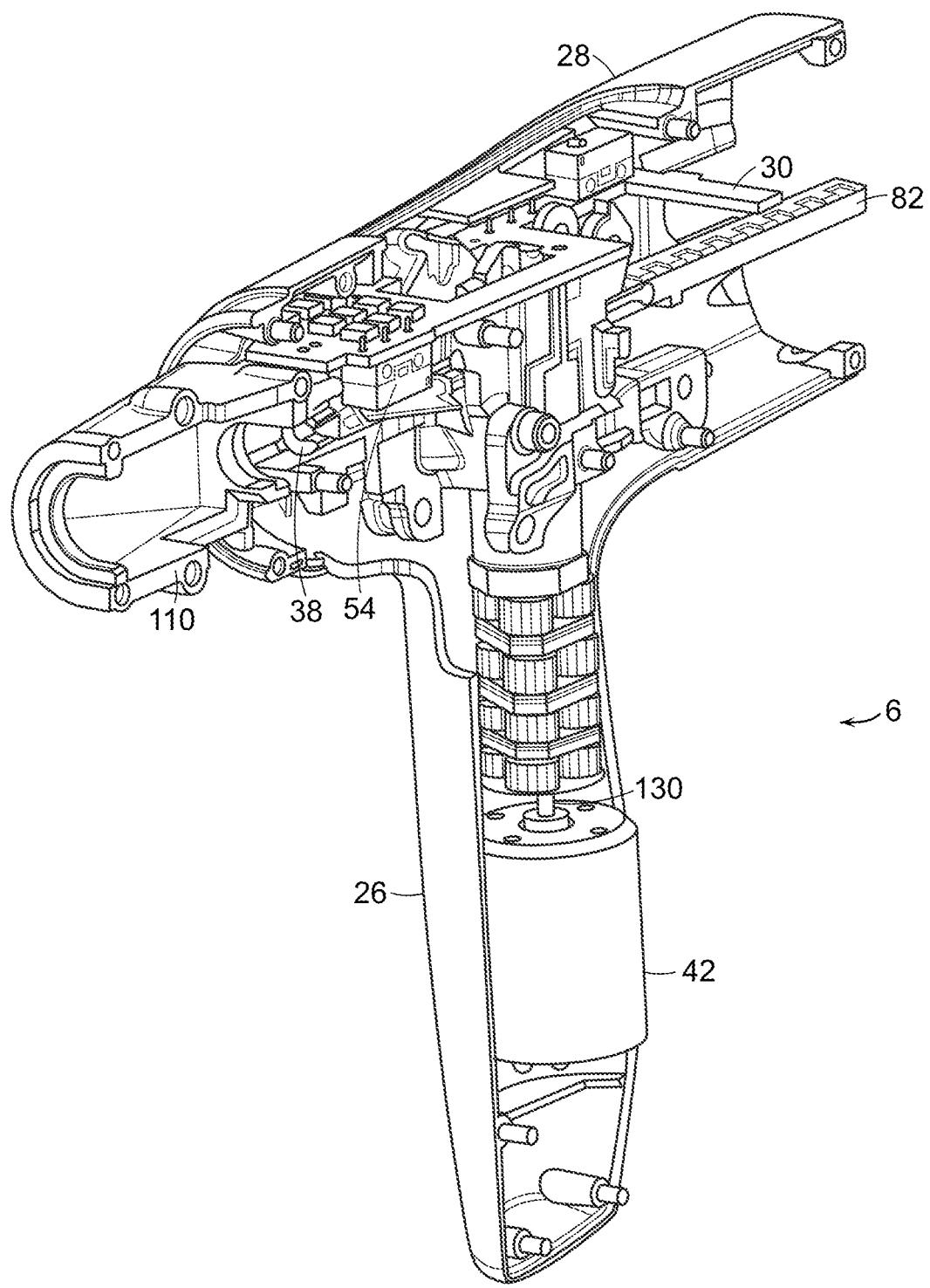
FIGS. 33-34 are front side perspective, cutaway views of the handle according to various embodiments.
Figure 34:
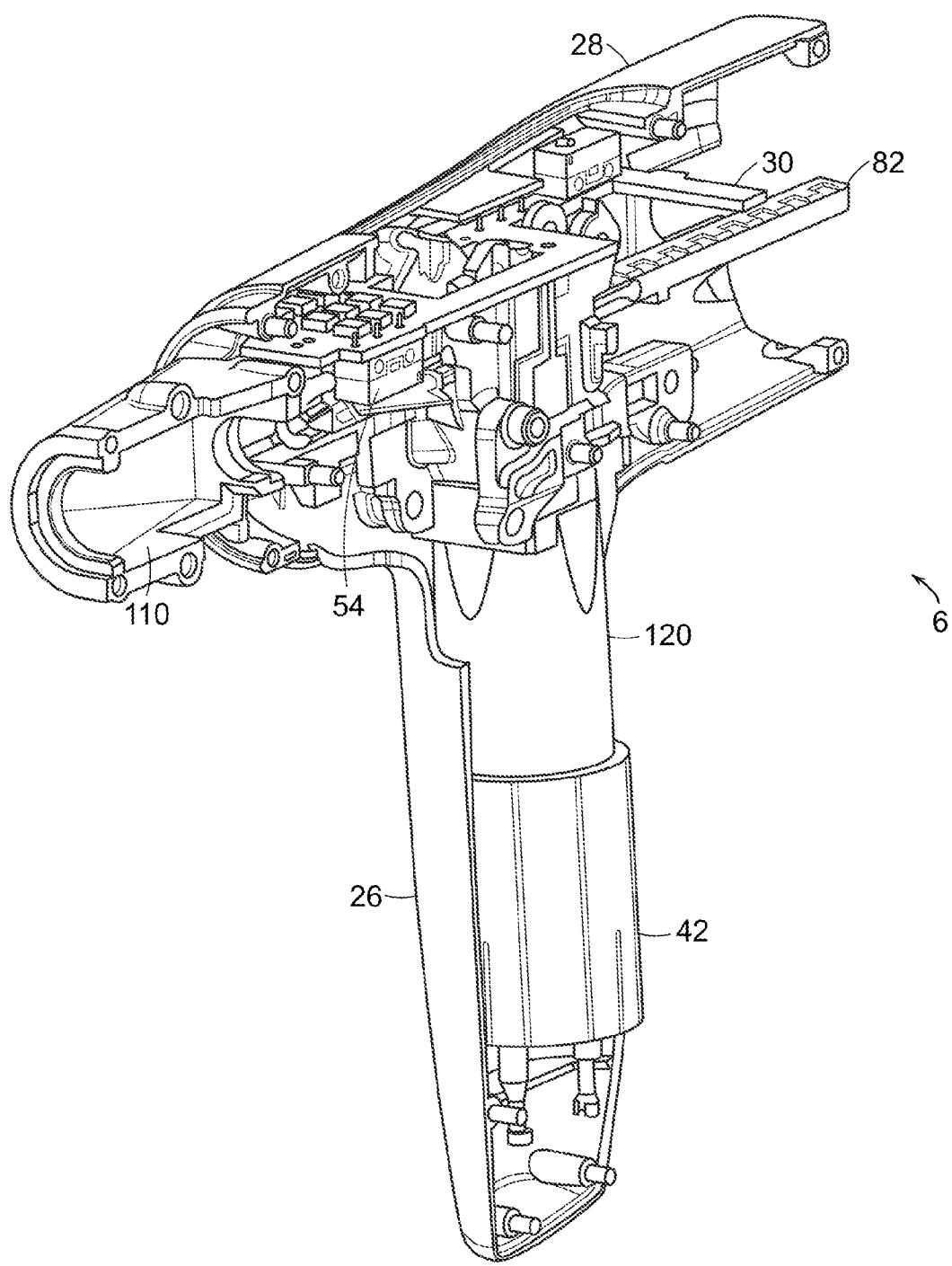
Figure 35:
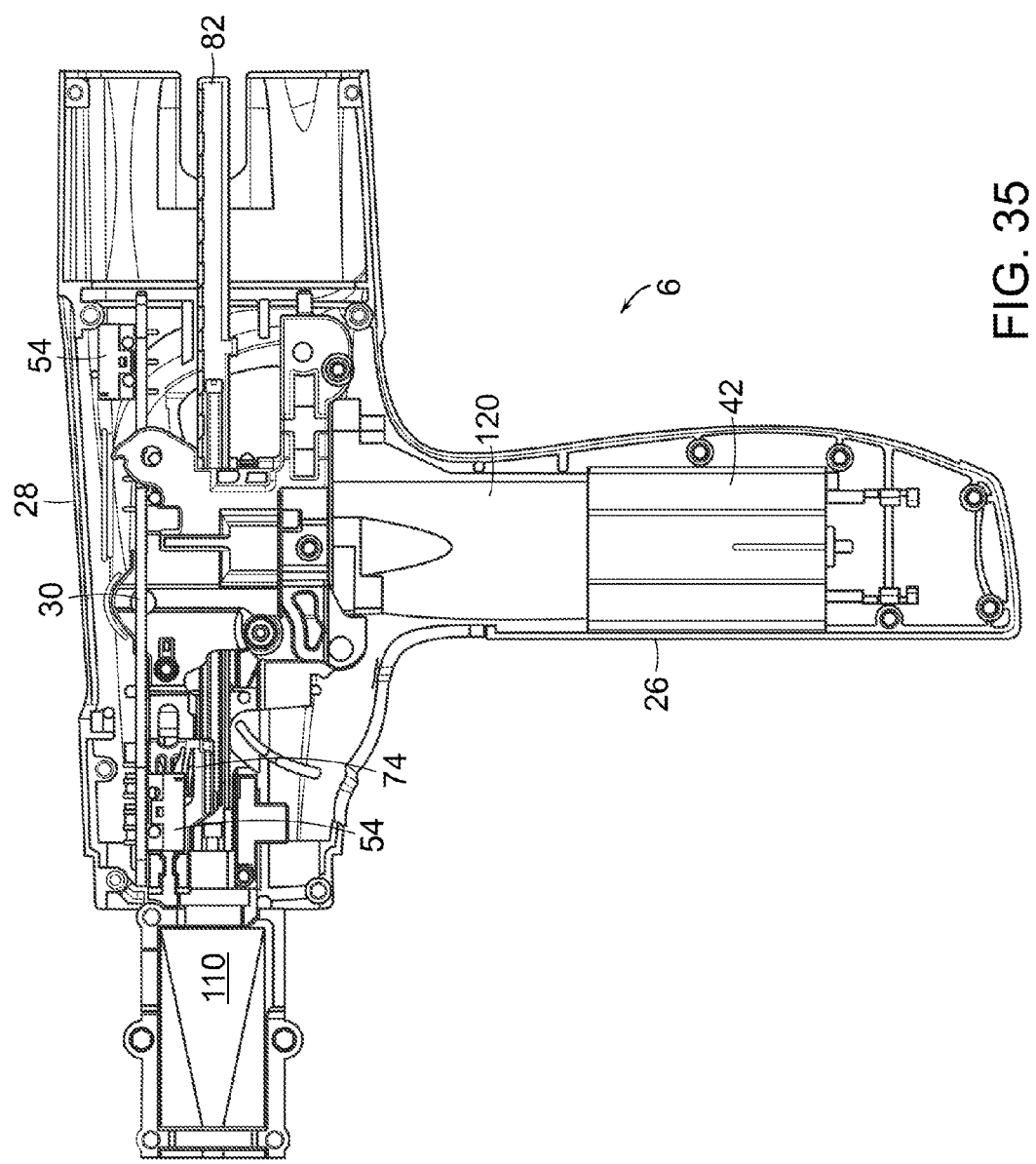
FIG. 35 is a front side view of the handle according to various embodiments.

FIG. 32 is a back side perspective view that shows the gear assembly 120 geared to the pinion 86 (without showing the frame 110). As shown in FIG. 32, the gear assembly 120 may comprise (i) an upper gear 122 that is geared to the pinion 86, and (ii) a lower gear assembly, covered by a lower gear assembly cover 124, that rotates the upper gear 122. The lower gear assembly may be coupled to the motor 42, as shown in FIGS. 33-35. These figures show the motor 42, with an output shaft 130, coupled to the gear assembly 120. As can be seen in these figures, the motor 42 may be positioned in the pistol grip portion 26 of the handle 6. These figures also show how the frame 110 fits into the upper portion 28 of the handle 6 according to various embodiments. The battery pack 44 (not shown in FIGS. 33-36) may be located in the pistol grip portion 26 of the handle 6 below the motor 42.

In addition, although in the embodiments describes above a pinion was used to longitudinally reciprocate the rack, other devices for longitudinally reciprocating the rack may be used in other embodiments. For example, a screw drive or other means may be used to longitudinally reciprocating the rack. Also, in other embodiments, the channel 80 of the rack 82 may comprise one or a number of wedges (or cams) that cause the slider 74 move generally perpendicular to the direction of movement of the rack 82 when the tab 96 of the slider 74 engages the wedge (or cam). In such embodiments, the perpendicular movement of the slider 74 (relative to the direction of movement of the rack 82) may actuate or deactuate the switch 54, depending on the location of the switch relative to the slider. In addition, in other embodiments, the rack 82 may comprise a cam and the slider 74 may comprise a cam follower. In such embodiments, longitudinal movement of the rack may induce eccentric motion in the slider 74, which may actuate or deactuate the switch 54, depending on the location of the switch relative to the slider.

Figure 40:
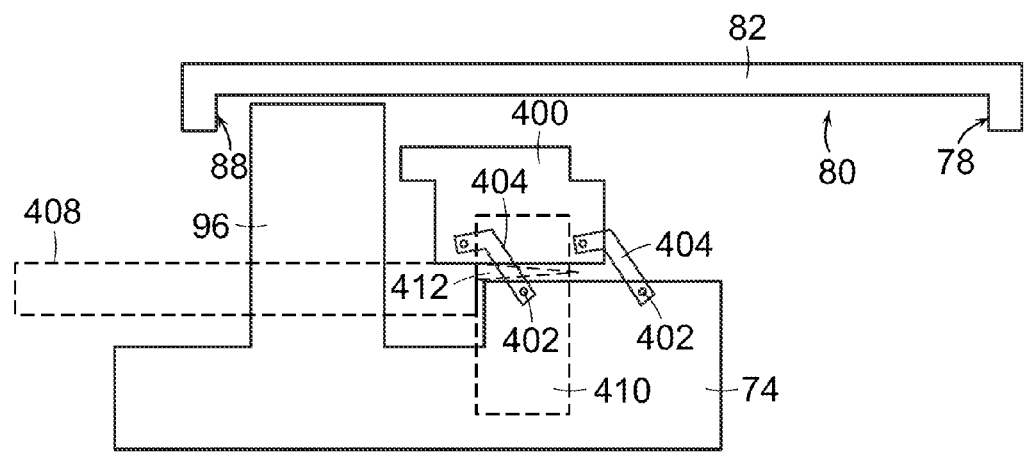

In other embodiments, the portion (e.g., the tab 96) of the slider 74 that engages or interfaces with the channel 80 may be dynamic, thereby allowing the rack 82, with a fixed channel length, to be used in instruments where the cutting stroke of the end effector 12 is different for different procedures. For example, the slider may have multiple interface portions (e.g., tabs) that are selectively used depending on the situation. This may be desirous, for example, where the end effector 12 permits cartridges of different length, requiring different lengths of cut by the cutting instrument in the end effector 12. In other embodiments, the shaft/end effector combination may be replaceable to accommodate uses requiring different lengths of cut by the cutting instrument in the end effector 12. For short cutting strokes, the reverse direction switch 54 needs to be actuated sooner in the cutting stroke that for longer cutting strokes. FIG. 40 is a diagram of such a slider 74 according to various embodiments. FIG. 40 is a top view of a portion of the slider 74 showing the tab 96 extending outwardly into the channel 80 defined by the drive member 82. Adjacent to the 96 is a moveable second tab 400 that is capable of pivoting about one or more pivot points 402 on the body of the slider 74. The slider body may be connected to the moveable second tab 400 by pivoting arms 404. The pivoting arms 404 may permit the second tab 400 to rotate pivotably toward the channel 80 such that the second tab 400 extends into the channel 80. When the second tab 400 is pivoted so that it extends into the channel 80, the proximate-side channel shoulder 78 contacts the second tab 400 first, urging the slider body 74 into the switch-actuating position as described above, at a time and length of traveled distance less than it would take the shoulder 78 to contact the tab 96 if the second tab 400 was not extending into the channel 80. In that way, when the second tab 400 is extended into the channel, the switch 54 can be actuated sooner in the cutting stroke than when the second tab 400 does not extend into the channel. That way, the drive member 82 can be used in procedures where a shorting cutting stroke is used, requiring sooner activation of the reverse motor switch 54.

In various embodiments, the second tab 400 can be pivoted into the channel 80 by force from a pusher 408 that engages a portion 410 of the second tab 400. For example, relative to the view of FIG. 40, the portion 410 may extend downwardly, into the page, from the second tab 400 and the pusher 408 may be located below (into the page) the slider body 74. The pusher 408 may be urged proximately when a short cutting stroke is needed, thereby causing the pusher 408 to engage the extending portion 410 of the second tab 400, thereby causing the second tab 400 to extend into the channel 400. The pusher 408 may also comprise a wedge portion 412 that wedges between the slider body 74 and the second tab 400 so that second tab 400 remains rotated/extended even when the shoulder 78 engages the tab 400. Yet the pusher 408 may move with the slider 74 so that the slider 74 can be moved to its switch-actuating position when the proximate-side shoulder 78 of the channel 80 engages the second tab 400. In another embodiment, the pusher 408 may be moved toward the drive member 82 (rather than proximately) to thereby move the second tab 400 toward the channel 80.

The pusher 408 may be activated mechanically (such as by an operator-actuated lever or different shaft that cause the pusher 408 to be actuated) magnetically (such as by a solenoid) electrically (such as shape memory materials that change shape with heat caused by electrical current), or any other suitable means.

In addition, in various embodiments, the operation and movement of the slider 74 may be overridden by a user of the instrument to permit, for example, early return (proximate movement) of the rack 82. For example, the instrument 10 may comprise an externally-accessible manual override control (such as a lever or switch) that, when actuated by the user, causes the motor to stop or reverse direction, regardless of the status of the slider 74. For example, in one embodiment, actuation of the externally-accessible manual override control may disengage the pinion 86 from the rack 82 so that the rack 82 is not driven by the pinion 86. The motor control circuit in such an embodiment may include circuit components that reverse the motor even if the slider 74 is not in its switch-actuating position.

Figure 38:
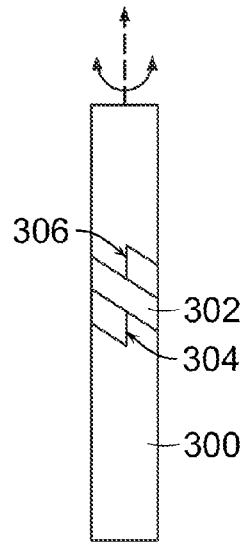
FIGS. 38-40 show drive members according to other various embodiments of the present invention.

In addition, in other embodiments, rather than using a longitudinally-moving drive member (e.g., rack 82), the instrument may comprise a rotating drive member that drives the slider 74 relative to the switch 54. For example, FIG. 38 is a diagram of a spirally rotating (i.e., rotating about the roll axis) drive member 300. As shown in FIG. 38, the drive member 300 defines a helical channel 302 having a first shoulder 304 at the proximate-side of the channel 302 and a second shoulder 306 at the distal-side of the channel 302. When the drive member 300 forwards rotates about its roll axis, the proximate-side shoulder 304 may engage the slider 74 to urge it to its switch-actuating position. Similarly, when the drive member 300 reverse rotates about its roll axis, the distal-side shoulder 306 may engage the slider 74 to urge it to its non-switch-actuating position. The drive member 300 may be rotated by the motor 42 using an appropriate gearing structure.

Figure 39:
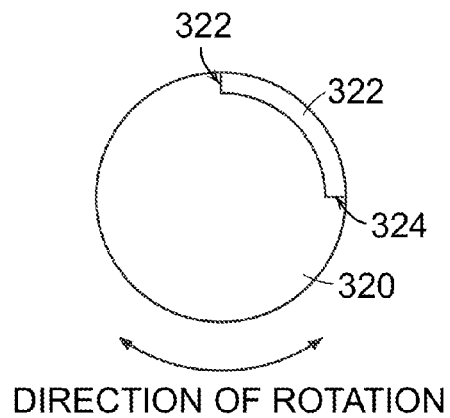

In another embodiment, as shown in FIG. 39, the drive member 320 may be circular or elliptical, such as disk-shaped, and rotate about its yaw axis. In such an embodiment, the disk-shaped drive member 320 may define a peripheral channel 322 that extend partially around the periphery of the drive member 320. The channel 322 comprises a first shoulder 324 at a first side of the channel 322 and a second shoulder 326 at a second side of the channel 322. When the drive member 320 rotates CCW about its yaw axis, the first shoulder 324 may engage the slider 74 to urge it to its switch-actuating position. Similarly, when the drive member 320 rotates CW about its yaw axis, the second side shoulder 326 may engage the slider 74 to urge it to its non-switch-actuating position. The drive member 320 may be rotated by the motor 42 using an appropriate gearing structure. In FIG. 39, the channel 322 is a 90 degree arc; it other embodiments arcs of different size may be used for the channel.

The surgical instruments disclosed herein can be designed to be disposed of after a single use, or they can be designed to be used multiple times. In either case, however, the device can be reconditioned for reuse after at least one use. Reconditioning can include any combination of the steps of disassembly of the surgical instrument, followed by cleaning or replacement of particular pieces, and subsequent reassembly. In particular, the surgical instrument can be disassembled, and any number of the particular pieces or parts of the device can be selectively replaced or removed in any combination. Upon cleaning and/or replacement of particular parts, the surgical instrument can be reassembled for subsequent use either at a reconditioning facility, or by a surgical team immediately prior to a surgical procedure. Those skilled in the art will appreciate that reconditioning of a surgical instrument can utilize a variety of techniques for disassembly, cleaning/replacement, and reassembly. Use of such techniques, and the resulting reconditioned surgical instrument, are all within the scope of the present application.

Preferably, the surgical instrument described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Therefore, in various embodiments, the present invention is directed to a surgical instrument that comprises: (i) a handle; (ii) an end effector connected to the handle; (iii) an electric motor in the handle for powering the end effector; (iv) a motor control circuit connected to the motor for controlling the motor; (v) a drive member that is driven by the motor; and (vi) a slider. The motor control circuit comprises a plurality of switches, including a first switch with a moveable (e.g., depressible) actuator (e.g., plunger). The drive member, when driven by the motor, cause movement of a moveable component in the end effector, and comprises a first shoulder at a first position and a second shoulder at a second position. The slider comprises a first portion and a second portion. The first portion extends interfaces the drive member such that the slider is moveable in a direction of movement of the drive member when either the first shoulder or the second shoulder of the rack engages the first portion. The second portion of the slider actuates the moveable actuator of the first switch when the drive member moves the slider to a first position relative to the first switch. In various embodiments, the motor control circuit does not comprise an integrated circuit.

In various implementations, the drive member is rotated by the motor, such as about a roll axis or yaw axis of the drive member. In other embodiments, the drive member is drive longitudinally by the motor. For example, in such embodiments, the drive member may comprise a rack that is geared to a pinion that the rotated by the motor, such that rotation of the motor cause the rack to move longitudinally. The rack moves the slider to the first position relative to the first switch when the rack is moved longitudinally in a first direction by the pinion such that the first shoulder engages the tab of the slider, the slider remains in the first position relative to the first switch when the rack is moved longitudinally in a second direction by the pinion that is opposite the first direction until the second shoulder of the rack engages the tab of the slider, and the slider moves out of engagement with the moveable actuator when the second shoulder of the rack moves the slider from the first position relative to the first switch to a second position relative to the first switch.

The surgical instrument may further comprise a frame inside the handle that comprises a stopper. The slider may comprise an upper arm and a lower arm that collectively define a U-channel. The U-channel may engage the stopper when the slider is moved to the first position relative to the first switch.

In yet other general embodiments, the present invention is directed to a device that actuates a switch having a moveable actuator, where the device comprise: (i) a longitudinally-moveable rack; and (ii) a slider that engages the rack such that longitudinally movement of the rack causes the slider to move relative to the switch such that the slider actuates the moveable actuator of the switch when the rack moves the slider to a first position relative to the switch. In various implementations, longitudinal movement of the rack may cause longitudinal, perpendicular, or eccentric movement of the slider.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical instrument, comprising:
    an end effector comprising a moveable component;
    an electric motor for powering the end effector;
    a moveable drive member that is driven in a first direction when the electric motor operates in a first direction and that is driven in a second direction when the electric motor operates in a second direction, wherein movement of the drive member causes movement of the moveable component of the end effector, and wherein the moveable drive member defines a channel; and
    a motor control circuit connected to the motor for controlling the motor, wherein the motor control circuit comprises a switching circuit that, upon actuation, reverses direction of the motor from the first direction to the second direction, wherein the switching circuit is actuatable separately through each of:
        actuation of a moveable switch actuator of the switching circuit through movement of the drive member at least in the first direction from a first switch actuator position to a second switch actuator position, wherein the moveable switch actuator comprises:
            a first portion that is disposed in the channel defined by the drive member; and
            a second portion that actuates a switch of the switching circuit when the drive member engages the first portion of the moveable switch actuator to move the moveable switch actuator from the first switch actuator position to the second switch actuator position; and
        manual actuation by a user of the surgical instrument.

2. The surgical instrument of claim 1, wherein the moveable component of the end effector comprises a moveable cutting instrument.

3. The surgical instrument of claim 1, wherein the switching circuit of the motor control circuit comprises:
    a first reverse switch that, upon manual actuation by a user, reverses direction of the electric motor; and
    a second reverse switch that comprises a depressible actuator, wherein actuation of the depressible actuator through movement of the drive member in the first direction reverses direction of the motor.

4. The surgical instrument of claim 3, further comprising:
    a handle, wherein the electric motor is positioned in the handle; and
    a circuit board in the handle, wherein the second reverse switch is mounted to the circuit board.

5. The surgical instrument of claim 4, further comprising a frame inside the handle, wherein:
    the circuit board is connected to the frame;
    the frame comprises a stopper;
    the moveable switch actuator defines a U-channel; and
    the U-channel engages the stopper when the moveable switch actuator is moved to the second switch actuator position relative to the second reverse switch.

6. The surgical instrument of claim 3, wherein the moveable switch actuator remains in the second switch actuator position relative to the second reverse switch until the drive member engages the moveable switch actuator to move the moveable switch actuator in the second direction from the second switch actuator position.

7. The surgical instrument of claim 6, wherein:
    the channel defined by the drive member comprises a first shoulder at a first end of the channel and a second shoulder at a second end of the channel; and
    the first portion of the moveable switch actuator interfaces with the drive member such that the moveable switch actuator is moveable by the drive member when either the first shoulder or the second shoulder of the drive member engages the first portion of the moveable switch actuator;

the second portion of the moveable switch actuator actuates the depressible actuator of the second reverse switch when the first shoulder of the drive member engages the first portion of the moveable switch actuator to move the first portion and the second portion of the moveable switch actuator from the first switch actuator position to the second switch actuator position relative to the second reverse switch; and the moveable switch actuator remains in the second switch actuator position relative to the second reverse switch until the second shoulder of the drive member engages the first portion of the moveable switch actuator to move the moveable switch actuator from the second switch actuator position to the first switch actuator position.

8. The surgical instrument of claim 7, wherein:

the drive member moves the moveable switch actuator to the second switch actuator position relative to the second reverse switch when the drive member is moved in the first direction such that the first shoulder engages the first portion of the moveable switch actuator;

the moveable switch actuator remains in the second switch actuator position relative to the first reverse switch when the drive member is moved in the second direction until the second shoulder of the drive member engages the first portion of the moveable switch actuator; and the moveable switch actuator moves out of engagement with the depressible actuator when the second shoulder of the drive member moves the moveable switch actuator from the second switch actuator position to the first switch actuator position.

9. The surgical instrument of claim 1, further comprising a pinion that is rotated by the electric motor, and wherein the pinion drives the drive member in the first direction when actuated by the electric motor.

10. The surgical instrument of claim 1, wherein:

the drive member rotates about a roll axis of the drive member when driven by the electric motor; and the channel defined by the drive member comprises a helical channel defined in the drive member.

11. The surgical instrument of claim 1, wherein:

the drive member rotates about a yaw axis of the drive member when driven by the electric motor; and the channel defined by the drive member comprises a peripheral channel that extends partially around a periphery of the drive member.

12. The surgical instrument of claim 1, wherein the motor control circuit comprises a plurality of switches, including the switching circuit, that are not embodied as part of an integrated circuit.

13. The surgical instrument of claim 7, wherein the motor control circuit comprises a plurality of switches, including the switching circuit, that are not embodied as part of an integrated circuit.

* * * * *